(12) United States Patent
Pinter

(10) Patent No.: US 9,938,325 B2
(45) Date of Patent: Apr. 10, 2018

(54) HIV-1 ANTIGENS WITH DISCRETE CONFORMATIONAL FORMS IN THE V1/V2 DOMAIN AND METHODS OF USE THEREOF

(71) Applicant: Rutgers, The State University of New Jersey, New Brunswick, NJ (US)

(72) Inventor: Abraham Pinter, Brooklyn, NY (US)

(73) Assignee: Rutgers, The State University of New York, New Brunswick, NJ (US)

( * ) Notice: Subject to any disclaimer, the term of this patent is extended or adjusted under 35 U.S.C. 154(b) by 0 days.

(21) Appl. No.: 14/426,646

(22) PCT Filed: Sep. 6, 2013

(86) PCT No.: PCT/US2013/058433
§ 371 (c)(1),
(2) Date: Mar. 6, 2015

(87) PCT Pub. No.: WO2014/039775
PCT Pub. Date: Mar. 13, 2014

(65) Prior Publication Data
US 2016/0257720 A1    Sep. 8, 2016

Related U.S. Application Data

(60) Provisional application No. 61/697,979, filed on Sep. 7, 2012.

(51) Int. Cl.
| | |
|---|---|
| C07K 16/16 | (2006.01) |
| C07K 14/005 | (2006.01) |
| C07K 14/16 | (2006.01) |
| A61K 39/12 | (2006.01) |
| A61K 39/00 | (2006.01) |

(52) U.S. Cl.
CPC .......... *C07K 14/005* (2013.01); *A61K 39/12* (2013.01); *C07K 14/162* (2013.01); *A61K 39/00* (2013.01); *C07K 2319/00* (2013.01); *C07K 2319/036* (2013.01); *C07K 2319/21* (2013.01); *C07K 2319/70* (2013.01); *C12N 2740/13011* (2013.01); *C12N 2740/16122* (2013.01); *C12N 2740/16134* (2013.01)

(58) Field of Classification Search
CPC .......... C07K 14/162; C07K 2319/036; C07K 2319/21; C07K 2319/00; C12N 2740/13011; C12N 2740/16134; C12N 2740/16122
See application file for complete search history.

(56) References Cited

U.S. PATENT DOCUMENTS

| | | | |
|---|---|---|---|
| 6,703,199 B1 | 3/2004 | Koide | |
| 6,815,201 B2* | 11/2004 | Pinter | A61K 39/12 |
| | | | 435/339.1 |
| 2003/0105282 A1* | 6/2003 | Pinter | A61K 39/21 |
| | | | 530/350 |
| 2004/0224308 A1 | 11/2004 | Binley et al. | |
| 2014/0335126 A1* | 11/2014 | Haynes | A61K 39/12 |
| | | | 424/208.1 |

FOREIGN PATENT DOCUMENTS

WO       2002/032925       4/2002

OTHER PUBLICATIONS

HIV Sequence Compendium, 2011, Alignment of HIV-1/SIVcpz Proteins, Kuiken, C., et al., eds., Published by Theoretical Biology and Biophysics Group, Los Alamos National Laboratory, NM, LA-UR 11-11440, pp. 350-353.*
Kayman, S. C., et al., Jan. 1994, Presentation of native epitopes in the V1/V2 and V3 regions of human immunodeficiency virus type 1 gp120 by fusion glycoproteins containing isolated gp120 domains, J. Virol. 68(1):400-410.*
Jobes, D. V., et al., 2006, High incidence of unusual cysteine variants in gp120 envelope proteins from early HIV type 1 infections from early HIV type 1 infections from a phase 3 vaccine efficacy trial, AIDS Res. Human Retrovir. 22(10):1014-1021.*
Barouch, D. H., 2008, Challenges in the developmen of an HIV-1 vaccine, Nature 455:613-619.*
Walker, B. D., and D. R. Burton, 2008, Toward an AIDS vaccine, Science 320:760-764.*
West, Jr., et al., 2014, Structural insights on the role of antibodies in HIV-1 vaccine and therapy, Cell 156:633-648.*
Zolla-Pazner, S, 2014, A critical question for HIV vaccine development: Which antibodies to induce?*
Go, E. P., et al., 2011, Analysis of the disulfide bond arrangement of the HIV-1 envelope protein CON-S gp140 deltaCFI shows variability in the V1 and V2 regions, J. Proteome Res. 10:578-591, published online Nov. 29, 2010.*
International Preliminary Report on Patentability issued in Application No. PCT/US213/058433 dated Mar. 10, 2015.
Interntional Search Report issued in Application No. PCT/US213/058433 dated Feb. 10, 2014.
Cicala et al., "The integrin alpha4beta7 forms a complex with cell-surface CD4 and defines a T-cell subset that is highly susceptible to infection by HIV-1," Proc Natl Acad Sci USA, 2009, vol. 106, pp. 20877-20882.
Co et al., "Humanized antibodies for antiviral therapy," Proc Natl Acad Sci, 1991, vol. 88, pp. 2869-2873.
Haynes et al., "Immune-Correlates Analysis of an HIV-1 Vaccine Efficacy Trial," The New England Journal of Medicine, 2012, vol. 366, pp, 1275-1286.
He et al., "Efficient Isolation of Novel Human Monoclonal Antibodies with Neutralizing Activity Against HIV-1 from Transgenic Mice Expressing Human Ig Loci," J. Immunol., 2002, vol. 169, pp. 595-605.

(Continued)

*Primary Examiner* — Jeffrey Parkin
(74) *Attorney, Agent, or Firm* — Fox Rothschild LLP

(57) ABSTRACT

The present invention relates to a novel composition of HIV-1 Env proteins that contain structurally and immunologically distinct V1/V2 domains. Methods of isolating such proteins, and methods of using such proteins as immunogens, therapeutic agents, vaccines, and test compounds for use in identifying a HIV antiviral are also provided.

14 Claims, 20 Drawing Sheets

(56) References Cited

OTHER PUBLICATIONS

Figure 1:
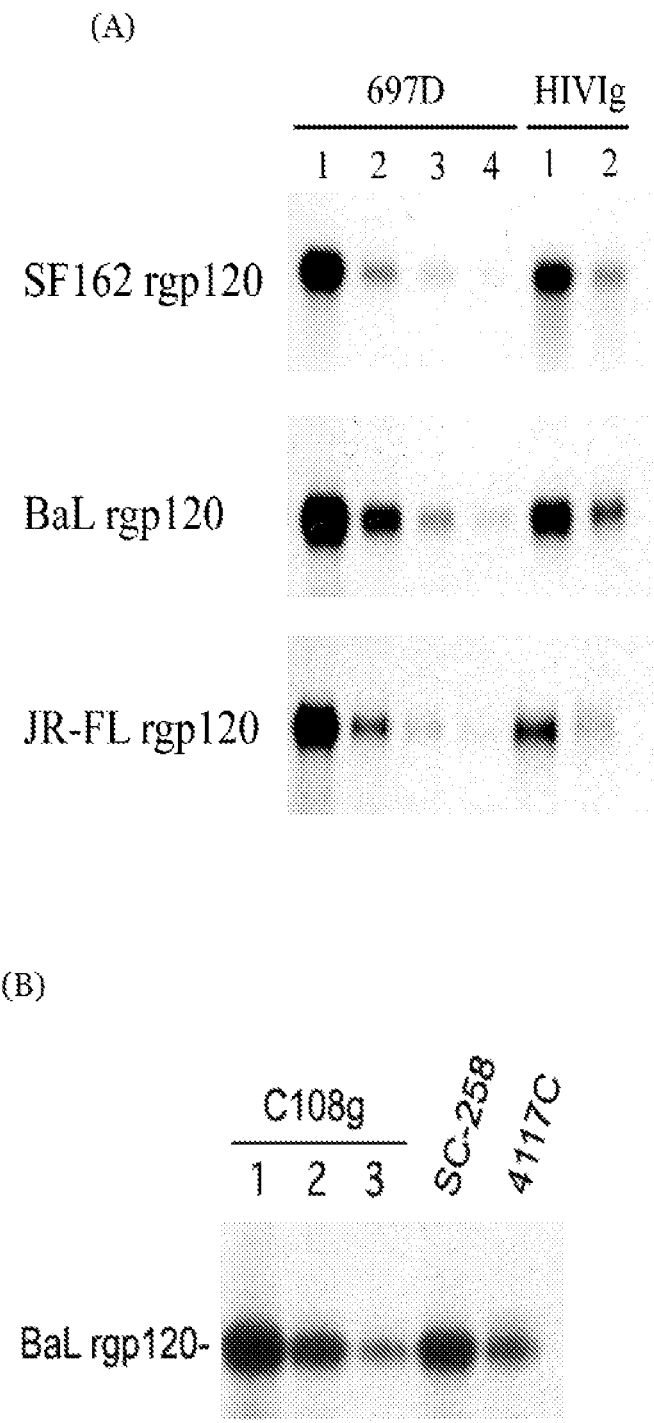

Jones et al., "Replacing the complementarity-determining regions in a human antibody with those from a mouse," Nature, 1986, vol. 321, pp. 522-526 (Abstract only).

Kohler and Milstein, "Continuous cultures of fused cells secreting antibody of predefined specificity," Nature, 1975, vol. 256, pp. 495-497.

Mark et al., "Derivation of Therapeutically Active Humanized and Veneered Anti-CD18 Antibodies," Metcalf and Dalton, Eds, Cellular Adhesion Molecular Definition to Therapeutic Potential, New York, Plenum Press, 1994, pp. 291-312 (Abstract only).

Moore et al., "Potent and broad neutralization of HIV-1 subtype C by plasma antibodies targeting a quaternary epitope including residues in the V2 loop," J Virol, 2011, vol. 85, pp. 3128-3141.

Nawaz et al., "The genotype of early-transmitting HIV gp120s promotes $\alpha 4\beta 7$ -reactivity, revealing $\alpha 4\beta 7$+/CD4+ T cells as key targets in mucosal transmission," PLoS Pathog., 2011, vol. 7, p. e1001301.

Rerks-Ngarm et al., "Vaccination with ALVAC and AIDSVAX to prevent HIV-1 infection in Thailand," N Engl J Med, 2009, vol. 361, pp. 2209-2220.

Verhoeyen et al., "Reshaping human antibodies: grafting an antilysozyme activity," Science, 1988, vol. 239, pp. 1534-1536 (Abstract only).

Walker et al., "Broad and potent neutralizing antibodies from an African donor reveal a new HIV-1 vaccine target," Science, 2009, vol. 326, pp. 285-289.

Fischer et al., "N-butyldeoxynojirimycin-mediated inhibition of human immunodeficiency virus entry correlated with changes in antibody recognition of V1/V2 region of gp120," Journal of Virology (1996); 70(10):7143-7152.

Go et al., "Analysis of the disulfide bond arrangement of the HIV-1 envelope protein CON-S gp140 DCFI shows variability in the V1 and V2 regions," Journal of Proteome REsearch (2001): 10:578-591.

* cited by examiner

Vaccine sera, obtained from the AIDS Vaccine Evaluation Group (AVEG), were from subjects immunized with the following antigens:

| Serum# | Antigen | Serum# | Antigen |
|---|---|---|---|
| 8, 12, 14 | HIVAC + rgp120 IIIB in Alum | 5, 6, 13, 16, 17, 19 | 300 mg rgp120 MN/IIIB in alum |
| 7 | 300 mg rgp120 MN in alum | 4, 20 | 300 mg rgp120 IIIB/ in alum |
| 10, 18 | 300 mg rgp120 IIIB in alum | 9, 11 | 100 mg QS21 + 300 mg rgp120 MN in alum |
| 15 | LWS (HIV-IIIB infected) | | |

Lanes 1-3 contain rodent Mabs SC-238 (lane 1), K10-A11 (lane 2) and K19B3 (lane 3)

35S Cys-labeled CaseA2 V1/V2 fusion protein was immunoprecipitated with sera at a dilution of 1:25 and precipitates were digested with PNGaseF prior to analysis by SDS-PAGE under non-reducing conditions.

FIGURE 9

| SEQ # | SEQ NAME | V1 FLANK | V1 HYPERVARIABLE | V2 Semiconserved | V2 HYPERVARIABLE | V2 FLANK |
|---|---|---|---|---|---|---|
| 7 | p3020/CaseA2 | AKLTPLCVTLNC | IDLRNATNATSNSNTTNTTSSSGGLMMEQG | EIKNCSFNITTSIRDKVQKEYALFYKLDIVP | IDNPKNSTN | YRLISCNTSVITQA |
| 8 | p2760/A244-PP | VKLTPPCVTLHCT | NANLTKANLTNVNNRTNVSNIIGNITD | EVRNCSFNMTTELRDKKQKVHALFYKLDIVP | IEDNNDSSE | YRLINCNTSVIKQP |
| 9 | p2800/CM244.ecI | VKLTPLCVTLHCT | NANLTKANLTNVNNRTNVSNIIGNITD | EVRNCSFNMTTELRDKKQKVHALFYKLDIVP | IEDNNDNSK | YRLINCNTSVIKQA |
| 10 | p2759/CM244.c01 | VKLTPLCVTLHCT | NANLTKANLTNVNNRTNVSNIIGNITD | EVRNCSFNMTTELRDKKQKVHALFYKLDIVP | IEDNNDSSE | YRLINCNTSVIKQA |
| 11 | p2809/1394C9.G1 | VKLTPLCVTLECT | NVTLKDTNGNSTSGNDTNVDNEKAINE | DMRNCSFNVTTVVRDKKKKENALFYKVDIVP | LFGDNSSM | YRLINCNTSTITQA |
| 12 | p2822/TV1c8.2.21 | VKLTPLCVTLNCT | ETNVTGNRTVIGNTNDTNIANATYKYE | EMKNCSFNVTTELRNKKHKEYALFYRLDIVP | LNENGDNSK | YRLINCNTSAITQA |
| 13 | p2799/9004S | VKLTPLCVTLNCS | QYVSSHVNNHNNSSHNVSSHSGNITS | DMKICSFNTTTEVRDKKQKVYSLFYKLDVVP | ISNDSSQ | YRLISCNTSAITQA |
| 14 | p2795/MN | VKLTPLCVTLNCT | DLRNTTNTNNTDNNNSKSEGTIKG | GEKNCSFNTTSIGDKMQKEYALLYKLDIVS | IDNDSTS | YRLISCNTSVITQA |
| 15 | p2824/C334.11 | VKLTPLCVTLNCT | KANLTSDTTNRTTGNRIDEVGNMTD | EVKNCTFNMTTELRDKKQKVHALFYKLDIVP | IKGNENSSGE | YRLINCNTSVIKQA |
| 16 | p2804/BJOX019 | VKLTPLCVTLNCT | NVNSNSSSNSSGNSNSTFENMQ | EMKNCSFNTTTELRDKKQKVYALFYRLDIVP | LSENSSE | YRLINCNTSAITQA |
| 17 | p2823/962M651 | VKLTPLCVTLNCT | EVNVTRNVNNSVVNNTTNVNNSMNG | DMKNCSFNITTELKDKKNVYALFYKLDIVS | LNETDDSETGNSSKY | YRLINCNTSALTQA |
| 18 | p2851/1051.12.C2 | VKLTPLCVTLNCT | DVNTNGTNNTTATTNSSGEIEEKG | EIKNCSFNVTSGIRDKMQKEYAFFYKLDIVP | IDNHSNNDSSSYRS | YRMISCNTSVITQA |
| 19 | p2830/BaL.21 | VKLTPLCVTLNCT | DLKNATNGNNNTNTTSSSGGMMGGG | EMKNCSFNITTNIRGKVQKEYALFYELDIVP | IDNKIDS | YRLISCNTSVITQA |
| 20 | p2802/BJOX028 | VKLTPLCVTLNCS | NAELTNLTNFNKTNVFKGIGNVTD | EVRNCSFNMTTLLTDKKQMVHALFYKLDIIQ | ISNSS | YRLINCNTSVIKQA |
| 21 | p2830/BaL.21 | VKLTPLCVTLNCT | DLKNATNGNNTNTTSSSGGMMGGG | EMKNCSFNITTNIRGKVQKEYALFYELDIVP | IDNKIDS | YRLISCNTSVITQA |
| 22 | p2849/1012.11 | VKLTPLCVTLNCT | DVTNATNINATNINNSSGGVESG | EIKNCSFNITTSVRDKVQKEYALFYKLDIVP | ITNESSK | YRLISCNTSVLTQA |
| 23 | p2860/CNE5 | VKLTPLCVTLHCT | TLNITNTTRNVTTPGPNLGNITD | EVRNCSFNVTTEIRDKHKHVNALFYKLDIVQ | IENNNNNSNK | YRLINCNTSVIKQA |
| 24 | p2568/92TH023 | VKLTPLCVTLNCT | NANVTNVKNITNVPNIIGNITD | EVRNCSFNMTTELRDKKQKVHALFYKLDIVP | IEDNTSSSE | YRLINCNTSVITQA |
| 25 | p2796/REJO4541 | VKLTPLCVTLKCT | DLNVTNSNSTDHSTNSSLEAKG | EIKNCSFNITTTPRDKQIQKEYAIFYKQDVVP | IKNDNIS | YRLINCNTSVITQA |
| 26 | p2794/620345.c01 | IKLTPLCVTLSCT | EAKFNETFNKIDNITKVSNLTD | EMRNCSFNMTTELRDKKQQVYALFYKLDIVP | IDNSSE | YRLINCNTSVITQA |
| 27 | p2825/QH0515 | VKLTPLCVTLNCT | DKLRNDTSGTNSSSWEKVQKG | EIKNCSFNITTGIRGRVQ-EYSLFYKLDVIP | IDSRNNSNNSTEFSS | YRLISCNTSVITQA |
| 28 | p2859/C2101.c01 | VRLTPLCVTLNCT | SANLTNVNNITYAPGIEKITD | EVRNCSFNMTTEIKDKKQKVSALFYKLDIVQ | INSSKNSSE | YRLINCNTSVIKQA |
| 29 | p2858/191084 | VKLTPLCVTLECT | AITNDTRGNETGINRTVETT | EMTNCSFNMTTELRDKKQKAYALFYKLDIVP | IGENSSSQ | YRLINCNTSVITQA |
| 30 | p2826/001428 | VKLTPLCVTLECT | QVNATQGNTTQVNVTQVNGD | EMKNCSFNITTSIRDKVQKEYALFYKLDVVP | LERENRGDSNSASK | YILINCNTSVITQA |
| 31 | p2836/ConB | AKLTPLCVTLNCS | DLKNNLLNTNSSGEKMEKG | EIKNCSFNITTSIRDKVQKEYALFYKLDVVP | IDNNNNTS | YRLISCNTSVITQA |
| 32 | p2806/BF1266 | VKLTPLCVTLNCS | DVPYNQSTKYNDNSTLYNR | EMKNCSFNATTEIKDKKKENALFYRLDVVP | LGESNSST | YRLINCNTSVVTQA |
| 33 | p2831/SHIV163P3 | VKLTPLCVTLHCT | NLENATNTTSSNWKEMNRG | EMKNCSFNVTTSIGNKMQKEYALFYKLDIVP | IDNDNTS | YNLINCNTSVITQA |
| 34 | p2798/WITO04160 | VKLTPLCVTLNCT | NVTISSTNGSTANVTMRE | EMKNCSFNTTTVIRDKIQKEYALFYKLDIVP | IEGKNTNTG | YRLINCNTSVITQA |
| 35 | p2805/Du156 | VKLTPLCVTLNCV | TYNNSMNSSATYNNSMNG | EIKNCSFNTTTELRDKKQKVYALFYRTDVVP | LNNNNNNSE | YILINCNTSTITQA |
| 36 | p2852/TT31P.2F10 | VKLTPLCVTLNCT | DELNNSNGTRVNITDKG | EIKNCSFNVTTAIRDKVQKTYALFYRLDVVP | IDDKHDNSSNNSSRK | YRLINCNTSVITQA |
| 37 | p2856/Ce7040100 | VKLTPLCVTLTCT | NAKNDNATVDGNSTTGG | EIKNCSFNITTELRDKKQRVHALFYRLDIVP | LNNSPREKGGSSSQ | YRLINCNTSAITQT |
| 38 | p2797/RHPA4258 | VKLTPLCVTLNCT | DLVNSNITRVDNTTEK | EMKNCSFNVTSGIRDKVQKEYALLYKLDIVQ | IDNDNTSHRDNTS | YRLISCNTSVITQA |
| 39 | p2853/700010058 | VQLTPLCVTLNCT | ELNNNSTTTTNSSEGK | EMKNCSFNIPTSMQDKTKKEYALFYKLDIVK | IDDSNNSTNNST | YRLISCNTSVVTQA |
| 40 | p2855/Cell76.A3 | VKLTPLCVTLTCT | NTTVSNGSSNSNANFE | EMKNCSFNATTEIKDKKKNEYALFYKLDIVP | LNNSSGK | YRLINCNTSAIAQA |
| 41 | p2811/BJOX002 | VKLTPLCVTLECK | NVNSSSSDTKNGTDP | EMKNCSFNATTELRDRKQKVYALFYKLDIVP | LNEKNSSE | YRLINCNTSTITQA |
| 42 | p2832/SHIV1157 | VKLTSLCVTLKCS | NFTGKSNVTYKGDM | EVGNCSFNVTTEIRDKKVQKVYALFYRLDITP | LDDNSSE | YILNCNSSTITQA |
| 43 | p2863/SHIV1157mu | VKLTSLCVTLKCS | NFTGKSNVTYKGDM | EVGNCSFNVTTEIRDKKKVYALFYRLDITP | LDDNSSE | YILINCNSSTITQA |
| 44 | p2808/706010164 | VKLTPLCVTLNCT | TAIAHNASNQNIT | DMKSCSFNATTEIRDKKHKVQALFYKLDITP | LRENETNNSFTE | YRLINCNTSAITQA |
| 45 | p2850/62357.14 | VKLTPLCVTLNCR | NVTNATNNTYNE | GIKNCSFNITTERRGRKKTEYATFYETDLVL | INDDNTTS | YRLINCNTSAITQA |
| 46 | p2683/ConC | AKLTPLCVTLNCR | NVTNATNNTYNE | EIKNCSFNITTELRDKRQKVYSLFYRLDIVQ | LNENSSE | YRLINCNTSAITQA |
| 47 | p2827/Q23.17 | VKLTPLCVTLHCT | NVTSVNTTGDRE | GLKNCSFNMTTELRDKRQKVYSLFYRLDIVQ | INENQGSE | YRLINCNTSAITQA |
| 48 | p2857/Q842.d12 | VKLTPLCVTLDCN | NATSTNFTAKNEG | EIKNCSFNATTELRDKKKEYALFYRLDIVQ | INEDQGNSSNNK | YRLITCNTSAITQA |
| 49 | p2807/CAP210.2 | VKLTPLCVTLNCS | DATYNNGTNSTD | TMKICSFNATTELRDKKKEYALFYRLDIVP | LKNEESQNFSE | YILINCNTSTIAA |
| 50 | p2812/1086C | VKLTPLCVTLNCT | NVKGNESDTSE | VMKNCSFKATTELKDKKHKVHALFYKLDVVP | LNGNSSSSGE | YRLINCNTSAITQA |
| 51 | p2810/CNE20 | VKLTPLCVTLECG | NITTRKESMT | EMKNCSFNITTELRDRKQTVYALFYKLDIVP | LSGKNSSGY | YRLINCNTSAITQA |
| 52 | p2854/CAP45.2 | VKLTPLCVTLRCT | NATINGSLTE | EVKNCSFNITTELRDKKQKAYALFYRPDVVP | LNKNSPSGNSSE | YILINCNTSTITQA |

Figure 11

+PngaseF, Non-Reduced

CaseA2 gp70-V1/V2 sequence  (V1/V2 domain is red)

```
ATG GCG TGT TCA ACG CTC CCA AAA TCC CCT AAA GAT AAG ATT GAC CCG CGG GAC CTC CTA ATC CCC TTA ATT CTC TTC CTG TCT CTC AAA  < 90
 M   A   C   S   T   L   P   K   S   P   K   D   K   I   D   P   R   D   L   L   I   P   L   I   L   F   L   S   L   K
        10          20          30          40          50          60          70          80

GGG GCC AGA TCC GCA GCA CCC GGC TCC AGC CCT CAT CAC CAC CAT CAC GTC TAC AAC ATT ACC TGG GAA GTG ACC AAT GGG GAT CGG < 180
 G   A   R   S   A   A   P   G   S   S   P   H   H   H   H   H   V   Y   N   I   T   W   E   V   T   N   G   D   R
       100         110         120         130         140         150         160         170

GAG ACA GTA TGG GCA ATA TCA GGT AAC CAC CCT CTG TGG ACT TGG TGG CCA GTC CTC ACC CCA GAT TTG TGT ATG TTA GCT CTC AGT GGG < 270
 E   T   V   W   A   I   S   G   N   H   P   L   W   T   W   W   P   V   L   T   P   D   L   C   M   L   A   L   S   G
       190         200         210         220         230         240         250         260

CCG CCC CAC TGG GGG CTA GAG TAT CAG GCG CCC TAT TCC TCG CCC CCC CCT TGT TGC TCA GGG AGC AGC AGT GCA GGC < 360
 P   P   H   W   G   L   E   Y   Q   A   P   Y   S   S   P   P   G   P   P   C   C   S   G   S   S   S   A   G
       280         290         300         310         320         330         340         350

TGT TCC AGA GAC TGC GAC GAG CCC TTG ACC CTC CTC ACC CCT CGG TGC AAC ACT GCC TGG AAC AGA CTT AAG CTA GAC CAG GTA ACT CAT < 450
 C   S   R   D   C   D   E   P   L   T   S   L   T   P   R   C   N   T   A   W   N   R   L   K   L   D   Q   V   T   H
       370         380         390         400         410         420         430         440

AAA TCA AGT GAG GGA TTT TAT GTC TGC CCC GGG TCA CAT CGC CCC AAG TCC TGT GGA GGT CCA GAC TCC TTC TAC TGT GCC < 540
 K   S   S   E   G   F   Y   V   C   P   G   S   H   R   P   R   E   A   K   S   C   G   G   P   D   S   F   Y   C   A
       460         470         480         490         500         510         520         530

TCT TGG GGC TGC GAG ACA ACC GGT AGA GTA TAC ATC ACA GTG GAC AAC AAT CTC ACC ACT AGC < 630
 S   W   G   C   E   T   T   G   R   V   Y   W   K   P   S   S   S   W   D   Y   I   T   V   D   N   N   L   T   T   S
       550         560         570         580         590         600         610         620

CAG GCT GTC CAG GTA TGC AAA GAC AAT AAG TGG TGC AAT CCC TTG GCT ATC CAG TTT ACA AAC GCC GGG AAA CAG GTC ACC TCA TGG ACA < 720
 Q   A   V   Q   V   C   K   D   N   K   W   C   N   P   L   A   I   Q   F   T   N   A   G   K   Q   V   T   S   W   T
       640         650         660         670         680         690         700         710

ACT GGA CAC TAT TGG GGT CTA CGT CTT TAT GTC TCT GGG CGG GAC CCG GGG CTT ACT TTC GGG ATC CGA CTC AGA TAT CAA AAT CTA GGA < 810
 T   G   H   Y   W   G   L   R   L   Y   V   S   G   R   D   P   G   L   T   F   G   I   R   L   R   Y   Q   N   L   G
       730         740         750         760         770         780         790         800

CCT CGG GTC CCG ATA GGA CCG AAC CCC GTC CTG GCA GAC CAA CTT TCG CTC CCG CGA CCT AAT CCC CTA CCC AAA CCT GCC AAG TCT CCC < 900
 P   R   V   P   I   G   P   N   P   V   L   A   D   Q   L   S   L   P   R   P   N   P   L   P   K   P   A   K   S   P
       820         830         840         850         860         870         880         890
```

Figure 14

```
CCC GCT AGC GTA AAA TTA ACC CCA CTC TGT GTT ACT TTA AAT TGC ATT GAT TTA AGG AAT GCT ACT AGT AAT AGC AAT ACT  < 990
 P   A   S   V   K   L   T   P   L   C   V   T   L   N   C   I   D   L   R   N   A   T   N   S   N   T
        910         920         930         940         950         960         970         980

ACT AAT ACC ACT AGT AGC GGG GGA CTG ATG GAA CAA GGA GAA ATA AAA AAC TGC TCT TTC AAT ATC ACC ACA AGC ATA AGA GAT < 1080
 T   N   T   T   S   S   G   G   L   M   E   Q   G   E   I   K   N   C   S   F   N   I   T   T   S   I   R   D
        1000        1010        1020        1030        1040        1050        1060        1070

AAG GTA CAG AAA GAA TAT GCA CTT TTT TAT AAG CTT GAT ATA GTA CCA ATA GAT AAT CCT AAA AAT AGT ACC AAC TAT AGG TTG ATA AGT < 1170
 K   V   Q   K   E   Y   A   L   F   Y   K   L   D   I   V   P   I   D   N   P   K   N   S   T   N   Y   R   L   I   S
        1090        1100        1110        1120        1130        1140        1150        1160

TGT AAC ACC TCA GTC ATT ACA CAG GCC GGC GCC  < 1203         SEQID #4
 C   N   T   S   V   I   T   Q   A   G   A                 SEQID #5
        1180        1190        1200
```

Figure 14 (Continued)

FIGURE 15

P565 plasmid (11,256 bp)

TTGGGCTGCAGGTCGATCGACTCTAGAACCcaaaacgcgtatttcggacaaacacacCCGCTG
GAAAGGACCCTATACCGTCCTACTGACTACCCCCACCGCTCTCAAAGTAGACGGC
ATTGCAGCGTGGATCCACGCTGCCCACGTAAAGGCTGCCGACACCAGGATTGAGC
CACCAGCAGAATCGACATGGCGTGTTCAACGCTCCCAAAATCCCCTAAAGATAAGA
TTGACCCGCGGGACCTCCTAATCCCCTTAATTCTCTTCCTGTCTCTCAAAGGGGCC
AGATCCGCAGCACCCGGCTCCAGCCCTCACCATCACCACCATCACGTCTACAACA
TTACCTGGGAAGTGACCAATGGGGATCGGGAGACAGTATGGGCAATATCAGGCAA
CCACCCTCTGTGGACTTGGTGGCCAGTCCTCACCCCAGATTTGTGTATGTTAGCTC
TCAGTGGGCCGCCCACTGGGGGCTAGAGTATCAGGCCCCCTATTCCTCGCCCC
CGGGGCCCCCTTGTTGCTCAGGGAGCAGCGGGAGCAGTGCAGGCTGTTCCAGAG
ACTGCGACGAGCCCTTGACCTCCCTCACCCCTCGGTGCAACACTGCCTGGAACAG
ACTTAAGCTAGACCAGGTAACTCATAAATCAAGTGAGGGATTTTATGTCTGCCCCG
GGTCACATCGCCCCGGGAAGCCAAGTCCTGTGGAGGTCCAGACTCCTTCTACTG
TGCCTCTTGGGGCTGCGAGACAACCGGTAGAGTATACTGGAAGCCCTCCTCCTCT
TGGGACTACATCACAGTGGACAACAATCTCACCACTAGCCAGGCTGTCCAGGTAT
GCAAAGACAATAAGTGGTGCAATCCCTTGGCTATCCAGTTTACAAACGCCGGGAAA
CAGGTCACCTCATGGACAACTGGACACTATTGGGGTCTACGTCTTTATGTCTCTGG
GCGGGACCCGGGGCTTACTTTCGGGATCCGACTCAGATATCAAAATCTAGGACCT
CGGGTCCGATAGGACCGAACCCCGTCCTGGCAGACCAACTTTCGCTCCCGCGA
CCTAATCCCCTACCCAAACCTGCCAAGTCTCCCCCCGCTAGCGT<u>AAAATTA</u>ACCCC
ACTCTGTGTTACTTTAAATTGCATTGATTTAAGGAATGCTACTAATGCCACTAGTAAT
AGCAATACTACTAATACCACTAGTAGTAGCGGGGGACTGATGATGGAACAAGGAG
AAATAAAAAACTGCTCTTTCAATATCACCACAAGCATAAGAGATAAGGTACAGAAAG
AATATGCACTTTTTTATAAGCTTGATATAGTACCAATAGATAATCCTAAAAATAGTAC
CAACTATAGGTTGATAAGTTGTAACACCTCAGTCATTACACAGGCCGGCGCCTAAT
AGATCGATTAGTTCAATTTGTTAAAGACAGGATCTCAGTAGTCCAGGCTTTAGTCCT
GACTCAACAATACCACCAGCTAAAACCACTAGAATACGAGCCATGATAAATAAAAG
ATTTTATTTAGTTTCCAGAAAAGGGGGGAATGAAAGACCCCACCAAGTTGCTTAG
GGCGAGCTCGAATTCATTGATCATAATCAGCCATACCACATTTGTAGAGGTTTTACT
TGCTTTAAAAAACCTCCCACACCTCCCCCTGAACCTGAAACATAAAATGAATGCAAT
TGTTGTTGTTAACTTGTTTATTGCAGCTTATAATGGTTACAAATAAAGCAATAGCATC
ACAAATTTCACAAATAAAGCATTTTTTCACTGCATTCTAGTTGTGGTTTGTCCAAAC
TCATCAATGTATCTTATCATGTCTGGATCCTCTACGCCGGACGCATCGTGGCCGGC
ATCACCGGCGCCACAGGTGCGGTTGCTGGCGCCTATATCGCCGACATCACCGATG
GGGAAGATCGGGCTCGCCACTTCGGGCTCATGAGCGCTTGTTTCGGCGTGGGTAT
GGTGGCAGGCCCCGTGGCCGGGGACTGTTGGGCGCCATCTCCTTGCATGCACC
ATTCCTTGCGGCGGCGGTGCTCAACGGCCTCAACCTACTACTGGGCTGCTTCCTA
ATGCAGGAGTCGCATAAGGGAGAGCGTCGACCTCGGGCCGCGTTGCTGGCGTTT
TTCCATAGGCTCCGCCCCCTGACGAGCATCACAAAATCGACGCTCAAGTCAGA
GGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTT
CTCCCTTCGGGAAGCGTGGCGCTTTCTCATAGCTCACGCTGTAGGTATCTCAGTTC FIGURE 15 (continued)

```
GGTGTAGGTCGTTCGCTCCAAGCTGGGCTGTGTGCACGAACCCCCGTTCAGCCC
GACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGG
ACAGTATTTGGTATCTGCGCTCTGCTGAAGCCAGTtAcCTTCGGAAAAAGAGTTGGT
AGCTCTTGATCCGGCAAACAAACCACCGCTGGTAGCGGTGGTTTTTTTGTTTGCAA
GCAGCAGATTACGCGCAGAAAAAAGGATCTCAAGAAGATCCTTTGATCTTTTCTA
CGGGGTCTGACGCTCAGTGGAACGAAAACTCACGTTAAGGGATTTTGGTCATGAG
ATTATCAAAAGGATCTTCACCTAGATCCTTTTAAATTAAAAATGAAGTTTTAAATCA
ATCTAAAGTATATGAGTAAACTTGGTCTGACAGTTACCAATGCTTAATCAGTGAG
GCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATG
ATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCT
TCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCC
GCAGTGTTATCACTCATGGTTATGGCAGCACTGCATAATTCTCTTACTGTCATGCCA
TCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCG
CCACATAGCAGAACTTTAAAAGTGCTCATCATTGGAAAACGTTCTTCGGGGCGAAA
ACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGACGTCTAAGAAACCATTATTATCATGACATTAACCTAT
AAAAATAGGCGTATCACGAGGCCCTGATGGCTCTTTGCGGCACCCATCGTTCGTA
ATGTTCCGTGGCACCGAGGACAACCCTCAAGAGAAATGTAATCACACTGGCTCA
CCTTCGGGTGGGCCTTTCTGCGTTTATAAGGAGACACTTTATGTTTAAGAAGGTTG
GTAAATTCCTTGCGGCTTTGGCAGCCAAGCTAGATCCAGCTTTTTGCAAAAGCCTA
GGCCTCCAAAAAGCCTCCTCACTACTTCTGGAATAGCTCAGAGGCCGAGGCGGC
CTCGGCCTCTGCATAAATAAAAAAATTAGTCAGCCATGGGGCGGAGAATGGGCG
GAACTGGGCGGAGTTAGGGGCGGGATGGGCGGAGTTAGGGGCGGGACTATGGT
TGCTGACTAATTGAGATGCATGCTTTGCATACTTCTGCCTGCTGGGGAGCCTGGG
GACTTTCCACACCTGGTTGCTGACTAATTGAGATGCATGCTTTGCATACTTCTGCCT
GCTGGGGAGCCTGGGGACTTTCCACACCCTAACTGACACACATTCCACAGCCAAG
CTAGCTTGAATTAATTCCCGAGCCCTTCCAATACAAAACTAATTAGACTTTGAGTG
ATCTTGAGCCTTTCCTAGTTTTTGTATTGGAAGGGCTCGTCGCCAGTCTCATTGAG
AAGGCATGTGCGGACGATGGCTTCTGTCACTGCAAGGGGTCACAATTGGCAGAG
GGGCGGCGGTCTTCAAAGTAACCTTTCTTCTCCTGGCCGAGCCGAGAATGGGAGT
AGAGCCGACTGCTTGATTCCCACACCAATCTCCTCGCCGCTCTCACTTCGCCTCGT
TCTCGTGGCTCGTGGCCCTGTCCACCCCGTCCATCATCCCGCCGGCCACCGCTCA
```

FIGURE 15 (continued)

```
GAGCACCTTCCACCATGGCCACCTCAGCAAGTTCCCACTTGAACAAAAACATCAAG
CAAATGTACTTGTGCCTGCCCCAGGGTGAGAAAGTCCAAGCCATGTATATCTGGGT
TGATGGTACTGGAGAAGGACTGCGCTGCAAAACCCGCACCCTGGACTGTGAGCCC
AAGTGTGTAGAAGAGTTACCTGAGTGGAATTTTGATGGCTCTAGTACCTTTCAGTCT
GAGGGCTCCAACAGTGACATGTATCTCAGCCCTGTTGCCATGTTCGGGACCCCTT
CCGCAGAGATCCCAACAAGCTGGTGTTCTGTGAAGTTTTCAAGTACAACCGGAAG
CCTGCAGAGACCAATTTAAGGCACTCGTGTAAACGGATAATGGACATGGTGAGCA
ACCAGCACCCTGGTTTGGAATGGAACAGGAGTATACTCTGATGGGAACAGATGG
GCACCCTTTTGGTTGGCCTTCCAATGGCTTTCCTGGGCCCCAAGGTCCGTATTACT
GTGGTGTGGGCGCAGACAAAGCCTATGGCAGGGATATCGTGGAGGCTCACTACC
GCGCCTGCTTGTATGCTGGGGTCAAGATTACAGGAACAAATGCTGAGGTCATGCC
TGCCCAGTGGGAGTTCCAAATAGGACCTGTGAAGGAATCCGCATGGGAGATCAT
CTCTGGGTGGCCCGTTTCATCTTGCATCGAGTATGTGAAGACTTTGGGGTAATAGC
AACCTTTGACCCCAAGCCCATTCCTGGGAACTGGAATGGTGCAGGCTGCCATACC
AACTTTAGCACCAAGGCCATGCGGGAGGAGAATGGTCTGAAGTAAGTAGCTTCCT
CTGGAGCCATCTTTATTCTCATGGGGTGGAAGGGCTTTGTGTTAGGGTTGGGAAA
GTTGGACTTCTCACAAACTACATGCCATGCTCTTCGTGTTTGTCATAAGCCTATCGT
TTTGTACCCGTTGGAGAAGTGACAGTACTCTAGGAATAGAATTACAGCTGTGATAT
GGGAAAGTTGTCACGTAGGTTCAAGCATTTAAAGGTCTTTAGTAAGAACTAAATACA
CATACAAGCAAGTGGGTGACTTAATTCTTACTGATGGGAAGAGGCCAGTGATGGG
GGTCTTCCCATCCAAAAGATAATTGGTATTACATGTTGAGGACTGGTCTGAAGCAC
TTGAGACATAGGTCACAAGGCAGACACAGCCTGCATCAAGTATTTATTGGTTTCTT
ATGGAACTCATGCCTGCTCCTGCCCTTGAAGGACAGGTTTCTAGTGACAAGGTCA
GACCCTCACCTTTACTGCTTCCACCAGGCACATCGAGGAGGCCATCGAGAAACTA
AGCAAGCGGCACCGGTACCACATTCGAGCCTACGATCCCAAGGGGGGCCTGGAC
AATGCCCGTCGTCTGACTGGGTTCCACGAAACGTCCAACATCAACGACTTTTCTGC
TGGTGTCGCCAATCGCAGTGCCAGCATCCGCATTCCCCGGACTGTCGGCCAGGA
GAAGAAAGGTTACTTTGAAGACCGCCGCCCTCTGCCAATTGTGACCCCTTTGCA
GTGACAGAAGCCATCGTCCGCACATGCCTTCTCAATGAGACTGGCGACGAGCCCT
TCCAATACAAAAACTAATTAGACTTTGAGTGATCTTGAGCCTTTCCTAGTTCATCCC
ACCCCGCCCCAGCTGTCTCATTGTAACTCAAAGTAGTTCATCCCACCCCGCCCCAG
CTGTCTCATTGTAACTCAAAGGGATGGAATATCAAGGTCTTTTTATTCCTCGTGCCC
AGTTAATCTTGCTTTTATTGGTCAGAATAGAGGAGTCAAGTTCTTAATCCCTATACA
CCCAACCCTCATTTCTTTTCTATTTAGCTTTCTAGTGGGGGTGGGAGGGGTAGGGG
AAGGGAACGTAACCACTGCTTCATCTCATCAGGAATGCATGTCCAGTAGGCAGAG
CTGCCACAGAGTGGGTGTATTTGTGGAGGAGGACTTTTTCTTCAGGACAGTTAAAA
GAGCAGGTCCACTGCTTGGATTGACAATTCCCCTATAGGTAGAGAGCTGCTAGTTC
TTCAGGTAAAACCAACTTTCTATTCCAAATGGAAGTTAGGTGAGGAGTAGTGGGAG
GAGTTCATGCCCTCCATGAAGACAGCTCAGTGTATCACCTGACAGATGGGTAGCC
CTACTGTAAAAGAAGGAAAGTTATTTCTGGGTCCTCCATTTATAACACAAAGCAGA
GTAGTATTTTTATATTTAAATGTAAAAACAAAAGTTATATATATGGATATGTGGATAT
ATGTGTATTTCTAATTGAGGAAACCATCCTAGTTACTGGGTTTGCCAAGTTTGAAGA
GCTTGGTTAACAAGAAAGGATCTCTTGAGTAGAGGTGGGGGTGCAGTACCAGGAA
AGGTGGTTATCTGGGGCTCAGCGCTTTATTACTATGTGGGGTTTCCCTGCCCACTC
```

FIGURE 15 (continued)

```
TGCAGGAGCAGATGCTGGACAGGTAGCAGGGTGGGACACCAGTGCTGCCACCAC
CTGTCCCTGTGCTTAGGCTAAGATGCATATGTATCCACACAGAGTTAGCAGGATGG
AGTTGGCTGGTCAACTTGAACATTGTTACTGATAGGGGTGGGTGGGGTTTATTTTT
TGGTGGGACTAGCATGTCACTAAAGCAGGCCTTTTGATATATTAAATTTTTTAAAGC
AAAACAAGTTCAGCTTTTAATCAACTTTGTAGGGTTTCTAACTTTACAGAATTGCCT
GTTTGTTTCAGTGTCTCCATCCACTTGCTCTTGGAGGAACGGAGGACAGGCAGAC
CTGGAGTTAAAACATTTGTCATTTTGTGTCATAGTGTCTACTTTCTCCCAGCAGAAT
ATTCCTTTCCTTCTTAGGAGTCCTATGGAGTTTTGTTTTGTTTTTTTCTATTACGAT
AAACATACCCCACCTCCATTCTGGCTTGCCCTGCTGTTCTCTGGTTGTTTGTGTGC
TGTCCGCAGCAGGCTGCCTGTGGTTTTCTCTTGCCATGACGACTTCTAATTGCCAT
GTACAGTATGTTCAGTTAGATAACTCCTCATTGTAAACAGACTGTAACTGCCAGAG
CAGCGCTTATAAATCAACCTAACATTTATAAGATTTCCTCTTGACTTGTTTCTTTGTG
GTTGGGGGAGGAAGAAAAAAAAAAGCGTGCAGTATTTTTTGTTCCTTCATTTCCTA
TCAAAAGAAAGGGGAGTGGTTCTGTTTTGTTTACTCGCAAAATAAGCTAGCTTATCT
ATTGGCTTTTCTTTTTTTTTTTTTTTAAACGGGCTTTTCTTGTACCTATAATTTGG
GGTAAGGTGTGAGAGTTTTTATAGTTTTTTGAGACAGGGTCTTGGTGTATACCCTTG
GCTGGCCTGGAGCTAACTATGTAGACTGGGCTAGCCTTTAACTTGCAGTTCTGCTT
TCAATTAGGGTTTATACATTTAGTCTTGGCAATTCCTAGTTCCACGTTTAATCTCTTT
ACATTTCAAAGCAGTGTTATCTGAAGAGTTCAGGCGCAGAGTCAATTCAATAGAGT
TACACAAAAACCTAAAAAACAAGTTTTAAATACCAAGTTATGTTGGCCTGGCCACTT
TTCACAGCTGTCCACAACTCAATGTGACAAGGCTACAAATTGGATATACTAGAATTT
CCTGGTGATTTGGAACCCCTGCTTCATTTCCCGGAACCAGGGCTTTTGGTGACAGT
CCTAGCTTATCAGATTATTTAAAACAGTTACTCTTCCTGCCCTTCTTCCTGAGACCT
TTGTCCAGCTGCCATGAGCCATCTACACAGTACTTGCTTCCCTGTTGAAGTCACTG
AAGGCACATCAGCCCAAGACATAAAGGCTTGTCCCGGATTCACTAGCCTGGTGAA
CTTGTGGTTCTCTGATGTTTTGTCCTGTTTTGTTGTGATTTAGTCTCAAATTTCCCAG
CCTGGTTTGAAAATCTGGGCTCCCAGCCTTCAATAAGGAGGACTACAGATATGTAC
GACTGAGCCTTGATTCCAGCCTCATGTTTATACGTCTGTGCTCAGCTCCCTGAAGG
TTCCAGTTTGAAACTCAATAATCCAGGGGTCAGAAAGTCTTGATCTTATCCCCACA
GTATGGCACCAAGCCTGGCTGAGCCTTCTGACTTAGTCTGCCCTGTTGCTATTTAA
GCACTTTCTTCACTAGGCTAAAAATAAAAGGAGCTTCCTCCTTTGCCATGGCGCT
GTGCATGATAGGAAAAGGTAGCTATCTACTAGCATATTAACTCCACTGTTTTGCTT
TGTGTGTTTGGTTTTGAGGAAGGGTCTCAACTGTGTATCCCTGGCTGGCCTGGCC
GGATCTAGCTTCGTGTCAAGGACGGTGACTGCAGTGAATAATAAAATGTGTGTTTG
TCCGAAATACGCGTTTTGAGATTTCTGTCGCCGACTAAATTCATGTCGCGCGATAG
TGGTGTTTATCGCCGATAGAGATGGCGATATTGGAAAAATCGATATTTGAAAATATG
GCATATTGAAAATGTCGCCGATGTGAGTTCTGTGTAACTGATATCGCCATTTTCC
AAAAGTGATTTTTGGGCATACGCGATATCTGGCGATAGCGCTTATATCGTTTACGG
GGGATGGCGATAGACGACTTTGGTGACTTGGGCGATTCTGTGTCGCAAATATC
GCAGTTTCGATATAGGTGACAGACGATATGAGGCTATATCGCCGATAGAGGCGAC
ATCAAGCTGGCACATGGCCAATGCATATCGATCTATACATTGAATCAATATTGGCC
ATTAGCCATATTATTCATTGGTTATATAGCATAAATCAATATTGGCTATTGGCCATTG
CATACGTTGTATCCATATCATAATATGTACATTTATATTGGCTCATGTCCAACATTAC
CGCCATGTTGACATTGATTATTGACTAGTTATTAATAGTAATCAATTACGGGGTCAT
```

FIGURE 15 (continued)

TAGTTCATAGCCCATATATGGAGTTCCGCGTTACATAACTTACGGTAAATGGCCCG
CCTGGCTGACCGCCCAACGACCCCGCCCATTGACGTCAATAATGACGTATGTTC
CCATAGTAACGCCAATAGGGACTTTCCATTGACGTCAATGGGTGGAGTATTTACGG
TAAACTGCCCACTTGGCAGTACATCAAGTGTATCATATGCCAAGTACGCCCCTAT
TGACGTCAATGACGGTAAATGGCCCGCCTGGCATTATGCCCAGTACATGACCTTAT
GGGACTTTCCTACTTGGCAGTACATCTACGTATTAGTCATCGCTATTACCATGGTGA
TGCGGTTTTGGCAGTACATCAATGGGCGTGGATAGCGGTTTGACTCACGGGGATT
TCCAAGTCTCCACCCCATTGACGTCAATGGGAGTTTGTTTTGGCACCAAAATCAAC
GGGACTTTCCAAAATGTCGTAACAACTCCGCCCCATTGACGCAAATGGGCGGTAG
GCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGAT
CCAGCCTCCGCGGCCGGGAACGGTGCATTGGAACGCGGATTCCCCGTGCCAAGA
GTGACGTAAGTACCGCCTATAGAGTCTATAGGCCCACCCCTTGGCTTCTTATGCA
TGCTATACTGTTTTGGCTTGGGGTCTATACACCCCGCTTCCTCATGTTATAGGTG
ATGGTATAGCTTAGCCTATAGGTGTGGGTTATTGACCATTATTGACCACTCCCCTAT
TGGTGACGATACTTTCCATTACTAATCCATAACATGGCTCTTTGCCACAACTCTCTT
TATTGGCTATATGCCAATACACTGTCCTTCAGAGACTGACACGGACTCTGTATTTTT
ACAGGATGGGGTCTCATTTATTATTTACAAATTCACATATACAACACCACCGTCCCC
AGTGCCCGCAGTTTTTATTAAACATAACGTGGGATCTCCACGCGAATCTCGGGTAC
GTGTTCCGGACATGGGCTCTTCTCCGGTAGCGGCGGAGCTTCTACATCCGAGCCC
TGCTCCCATGCCTCCAGCGACTCATGGTCGCTCGGCAGCTCCTTGCTCCTAACAG
TGGAGGCCAGACTTAGGCACAGCACGATGCCCACCACCACCAGTGTGCCGCACA
AGGCCGTGGCGGTAGGGTATGTGTCTGAAAATGAGCTCGGGGAGCGGGCTTGCA
CCGCTGACGCATTTGGAAGACTTAAGGCAGCGGCAGAAGAAGATGCAGGCAGCT
GAGTTGTTGTGTTCTGATAAGAGTCAGAGGTAACTCCCGTTGCGGTGCTGTTAACG
GTGGAGGGCAGTGTAGTCTGAGCAGTACTCGTTGCTGCCGCGCGCCACCAGA
CATAATAGCTGACAGACTAACAGACTGTTCCTTTCCATGGGTCTTTCTGCAGTCAC
CGTCCTTGACACGAAGC (Seq. ID No. 3)

HIV-1 ANTIGENS WITH DISCRETE CONFORMATIONAL FORMS IN THE V1/V2 DOMAIN AND METHODS OF USE THEREOF

CROSS REFERENCE TO RELATED APPLICATION

The present application is a U.S. National Phase of International Application No. PCT/US2013/058433, filed on Sep. 6, 2013, which claims the benefit of U.S. Provisional Application Ser. No. 61/697,979, filed Sep. 7, 2012. The contents of the foregoing applications are incorporated herein by reference in their entirety.

GOVERNMENT INTERESTS

This invention was made with government support under grant numbers R01 AI-46383, R01 AI102718-01 and P01 AI-0888610 from the National Institutes of Health. The United States government has certain rights to this invention.

FIELD OF THE INVENTION

The present invention relates to a novel composition of recombinant HIV-1 Env proteins that contain structurally and immunologically distinct V1/V2 domains.

BACKGROUND OF THE INVENTION

Recent studies have shown a role for the V1/V2 domain of the HIV-1 ENV protein as a target in HIV-1 vaccines. A series of potent and broadly neutralizing monoclonal antibodies (MAbs) targeting a class of quaternary epitopes that were dependent on several positions in the V2 region were isolated in one study (Walker et al., 2009, Science 326:285-289; Moore et al., 2011, Journal of Virology 85:3128-3141). These antibodies react preferentially with native trimeric Env complexes. Further studies have shown that a small conserved sequence in the V2 domain interacted with α4β7 integrin, the mucosal homing receptor for activated T cells, and that this interaction strongly enhanced infection of those cells (Nawaz et al., 2011, PLoS Pathog 7:e1001301; Cicala et al., 2009, Proc Natl Acad Sci USA 106:20877-20882). A third finding came from the analysis of correlates of protection in the recently concluded RV144 vaccine trial conducted in Thailand, the first HIV vaccine trial that resulted in some protection against infection (Rerks-Ngarm et al., 2009, N Engl J Med 361:2209-2220). Protection in this trial was shown to correlate with an increased titer of antibodies that bound to a V1/V2 fusion protein, but not to any other factor analyzed, including avidity and titers of Env-specific IgG and IgA, viral neutralizing activity or levels of Env-specific CD4+ T cells (Haynes et al., 2012, The New England Journal of Medicine 366:1275-1286).

SUMMARY OF THE INVENTION

Figure 6:
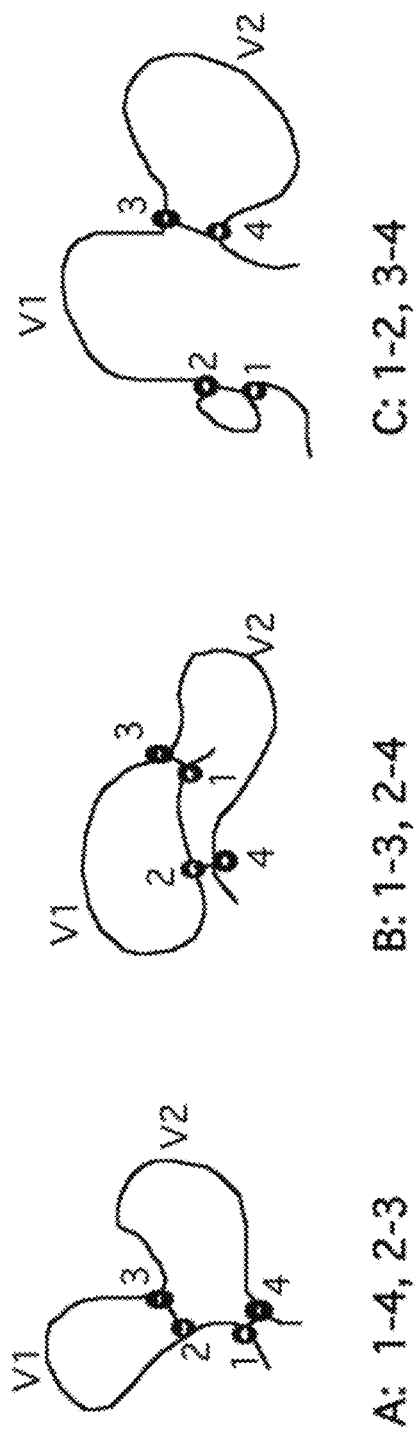
Figure 7:
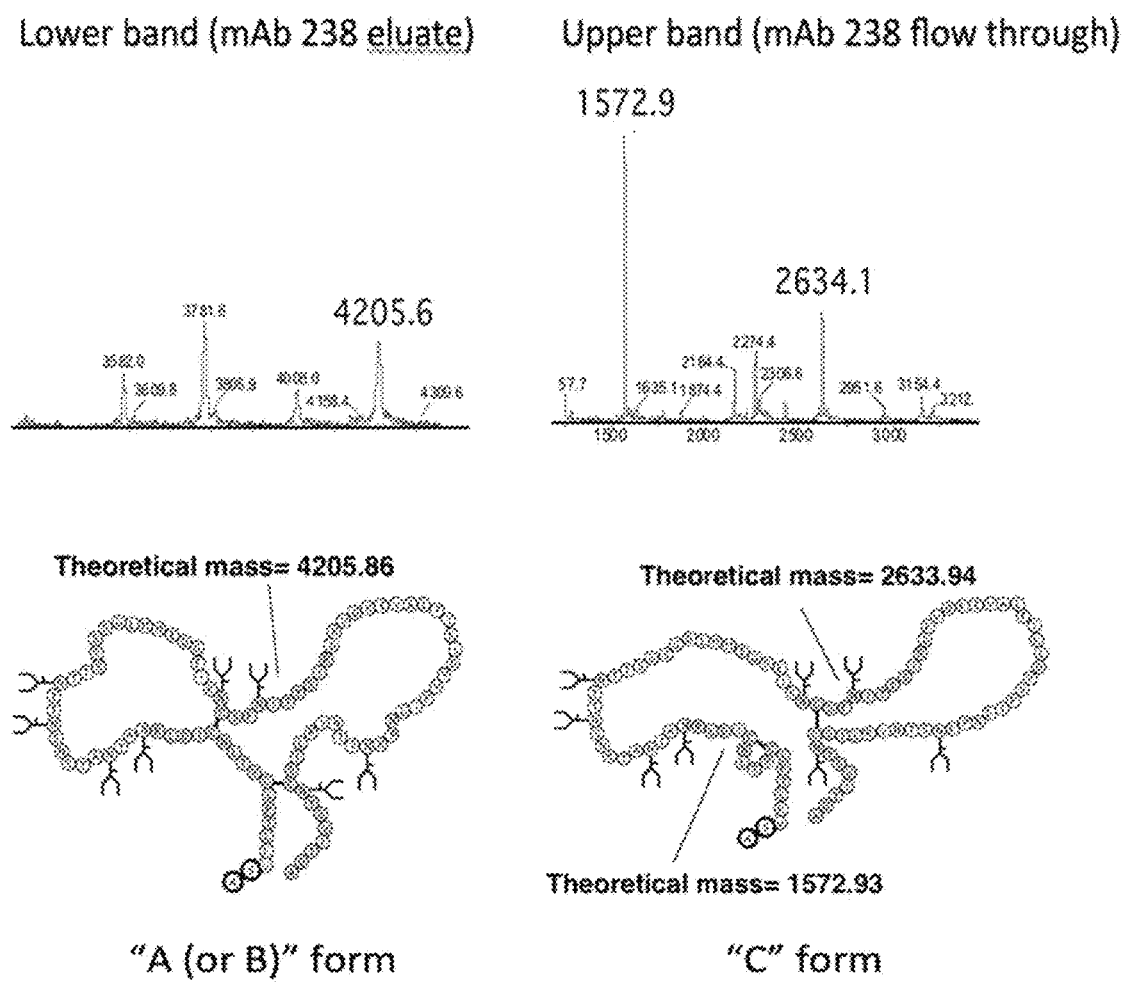

The present invention relates in part to isolated and purified polypeptides comprising the V1/V2 domain of a HIV envelope (Env) protein having a structural configuration of a "C" form, as at least shown in FIG. 6 and FIG. 7. As used herein, "HIV" is meant to represent either HIV-1 or HIV-2, and any and all subtypes thereof. Upon review of the specification, it will be understood that any such polypeptide is encompassed within the scope of invention which possesses the ability present and maintain the conformational integrity of the "C" form of the V1/V2 domain. It is disclosed herein that this "C" form presents one of several structural conformations based on an alternative form of disulfide bonding within this V1/V2 domain, which dramatically impacts the immunoreactivity of these proteins. To this end, an embodiment of the present invention further relates to a polypeptide which presents and maintains the conformational, antigenic, and immunoreactive integrity of the alternative "C" form of the V1/V2 domain, including but not limited to wherein the polypeptide is native gp120, or wherein the polypeptide native is gp140, or wherein the polypeptide is a recombinant form of gp120, or wherein the polypeptide is a recombinant form of gp140. Thus, another embodiment of the present invention further relates to such a polypeptide maintaining the structural integrity as discussed herein where the recombinant gp120-based form comprises a portion of the gp120 coding region, again, such that the antigenicity immunoreactivity of the V1/V2 structural configuration of the "C" form is maintained. A specific, but non-limiting embodiment of the present invention relates to such a presented polypeptide wherein the amino-terminal sequence represents a portion of MuLV gp70, including but not limited to a polypeptide presenting the "C" form which has the amino acid sequence as set forth in FIG. 14 (SEQ ID NO: 2). An additional embodiment of the present invention relates to nucleic acid molecules encoding a polypeptide with at least 90% amino acid sequence identity to a polypeptide which presents and maintains the conformational, antigenic, and immunoreactive integrity of the alternative "C" form of the V1/V2 domain, as well as related recombinant DNA molecules housing such a nucleic acid molecule, and any cell line transfected or transformed with any such recombinant DNA molecule.

The present invention also relates to isolated and purified polypeptides comprising the V1/V2 domain of a HIV envelope (Env) protein having a structural configuration of yet another form, identified herein as a "B" form, as at least shown in FIG. 6 and FIG. 7, or in the alternative, presented as both a "B" form and an "A" form (""B"/"A" form"). Again, upon review of the specification, it will be understood that any such polypeptide is encompassed within the scope of invention which possesses the ability to present and maintain the conformational integrity of the "B" form of the V1/V2 domain, or in the alternative a "B"/"A" combined form. Either form/forms as disclosed herein will again present one of several structural conformations based on an alternative form of disulfide bonding within this V1/V2 domain, dramatically impacting the immunoreactivity of these proteins. As disclosed immediately above in regard to the "C" forms, the present invention further relates to a polypeptide which presents and maintains the conformational, antigenic, and immunoreactive integrity of the alternative "B" form (or in the alternative a "B"/"A" combined form) of the V1/V2 domain, including but not limited to wherein the polypeptide is native gp120, native gp140, recombinant gp120, recombinant form gp140, a construction based upon a portion of the gp120 or gp 140 coding region, again, such that the antigenicity and immunoreactivity of the V1/V2 structural configuration of the "B" form (or in the alternative a "B"/"A" combined form) are maintained. An additional, but non-limiting embodiment of the present invention relates to such a presented polypeptide wherein the amino-terminal sequence represents a portion of MuLV gp70, including but not limited to a polypeptide presenting the "B" form (or a "B"/"A" combined form) which has the amino acid sequence as set forth in FIG. 14 (SEQ ID NO:2). An additional embodiment of the present invention relates to nucleic acid molecules encoding a polypeptide with at least 90% amino acid sequence identity to a polypeptide which presents and maintains the conformational, antigenic, and immunoreactive integrity of the alternative "B" form of the V1/V2 domain, or in the alternative a combined "B"/"A" form) as well as related recombinant DNA molecules housing such a nucleic acid molecule, and any cell line transfected or transformed with any such recombinant DNA molecule. It will be evident upon review of this specification that combinations of an "A" form, a "B" form and/or a "C" form are also contemplated herein as relating to the present invention.

The present invention also relates to utilizing the polypeptides of the present invention, including but not limited to polypeptides which maintain the conformational integrity disclosed herein as a "C" form, a "B" form and/or a combined "B/A" form in methods of treating a HIV positive subject which involves administering to such a subject a pharmaceutical composition comprising any such polypeptide disclosed herein, or combination thereof, with such a pharmaceutical composition optionally containing a pharmaceutically active carrier. It will be the goal of any such treatment to result in a reduction in the HIV viral load of a subject.

The present invention further relates to utilizing the polypeptides of the present invention, including but not limited to polypeptides which maintain the conformational integrity disclosed herein as a "C" form, a "B" form and/or a combined "B/A" form in methods of vaccinating a human subject against infection or progression of HIV which comprises administration of a pharmaceutical composition comprising any, or combination thereof, of such polypeptides disclosed herein, with the pharmaceutical composition optionally containing a pharmaceutically active carrier, wherein administration of the pharmaceutical composition results in generation of an immune response against HIV infection.

To this end, the present invention relates to any such methodology utilized to induce an enhanced immunological response against a HIV antigen in a mammalian host, wherein the mammalian host is inoculated with a polypeptide disclosed herein as a "C" form, a "B" form and/or a combined "B/A" form and, optionally, a pharmaceutically acceptable carrier. Thus, the present invention also relates to any such pharmaceutical composition which comprises an effective amount of such a polypeptide and, optionally, a pharmaceutically acceptable carrier.

Another embodiment relates to methods of identifying an HIV antiviral compound, which comprises the steps of: (a) combining component (i)—a test compound, component (ii)—a "C" form-specific antibody, or a "B" form-specific antibody and/or an antibody which specifically recognizes a combination of the "B" and "A" form, and component (iii)—a polypeptide of "C" form, a "B" form and/or a combined "B/A" form; (b) measuring the effect the test compound has on the affinity of component (ii) for component (iii) of step (a); and, (c) comparing the effect the test compound has on the affinity of component (ii) for component (iii) versus the affinity of component (ii) for component (iii) in the absence of the test compound. Such methods may utilize test compounds selected from the group consisting of a peptide, a protein, a non-proteinaceous organic or inorganic molecule, DNA and RNA.

BRIEF DESCRIPTION OF THE FIGURES

FIG. 1. Evidence of structural/immunological heterogeneity of the V1/V2 domain was seen for several rgp120s upon sequential radioimmunoprecipitations. (a) Analyses by sequential immunoprecipitations revealed that a substantial fraction (~25%) of three rgp120s tested were non-reactive with 697D, directed against a conformational V2 epitope. (b) C108g is a mAb isolated from an HIV-infected chimp that recognizes a glycan-dependent V1/V2 epitope overlapping with the PG9/PG16 site and possesses potent neutralizing activity against a limited set of viruses. C108g also recognized only a fraction of BaL rgp120 containing the correctly-folded V2 domain.

FIG. 2. To facilitate the structural analysis of the native V1/V2 domain, this region of a primary clade B Env (CaseA2) sequence was expressed as a fusion protein, joined to an N-terminal fragment of the MuLV Env protein, gp70. This fusion protein system allowed the expression of the V1/V2 domain as a native glycosylated and disulfide-bonded protein. Antibody reactivity with this V1/V2 fusion protein was the only variable shown to have a significant inverse correlation with risk of infection in the Thailand RV144 vaccine.

FIG. 3. Separation of the V1/V2 domain from the gp70 domain by cleavage at a proteolytic site engineered between the two domains shows that these regions form distinct and independent folded domains.

FIG. 4. The deglycosylated gp70-V1/V2$_{CaseA2}$ protein is resolved as a doublet by SDS-PAGE under non-reducing conditions, indicating distinct conformational forms.

FIG. 5. The two V1/V2 conformational forms possess distinct immunoreactivities with V1/V2-specific mAbs. Mabs isolated from infected humans and mice immunized with rgp120 all specifically recognize the V1/V2 lower band form. Mabs from rats immunized with V1/V2 fusion protein recognize upper band or both bands.

FIG. 6. Three V1/V2 conformers can exist, which differ in their disulfide bond patterns. Structure A was determined for the H XB2 strain of HIV gp120 by Leonard et al., 1990, J. Biol. Chem. 265:10373-10382.

FIG. 7. Homogeneous conformational forms of the V1/V2 fusion protein were isolated by immunoaffinity chromatography and analyzed by mass spectrometry. The two forms were fractionated by immunoaffinity on columns containing lower band-specific mab 238. The flow-through contained upper band forms, while the column eluate contained the lower band form. The upper band form contained peptides at mass of 1573 and 2634 predicted for the C form, while the lower band form contained the complex peptide with mass of 4206 characteristic of forms A and B.

FIG. 8. Analysis of alternate V1/V2 conformeric forms of the CaseA2 and BaL V1/V2 fusion proteins. For the CaseA2 protein, rat Mab K10A11 (directed against a site in the gp70 carrier domain) pulls down both forms, mouse Mab SC-258 recognizes only lower form and human Mab 8.22.2 (from immunized Xenomouse, which contained only human Ig genes) recognized predominantly upper band form. The two forms were also seen for BaL V1/V2 fusion protein, although they were nor resolved as well. Again, K10A11 recognized both bands, rat Mab 10/76b, directed against a linear V2 epitope, recognized both upper and lower band equally well, while chimp Mab C108g recognizes only the lower band form. The C108g epitope was not well-expressed in this protein, perhaps because of its glycan-dependence.

FIG. 9. Analysis of reactivity of human vaccine sera with conformers of the gp70-V1/V2$_{CaseA2}$ protein.

FIG. 10. Titrations of HIV-1-positive human immune sera show different patterns against specific V1/V2 conformers.

FIG. 11. Alignment of V1/V2 region of sequences analyzed in FIG. 12. Indicated are plasmid numbers and corresponding names of Envs these sequences were obtained from. Sequences (SEQ ID NOs: 7-48) are divided to indicate different regions of the V1/V2 domain; the conserved flanking regions, the V1 hypervariable region, the semi-conserved V2 region, the V2 hypervariable region and the V2 flank. The sequences are arranged by decreasing size of the V1 hypervariable region, and this order is reflected in the gel shown in FIG. 12.

Figure 12:
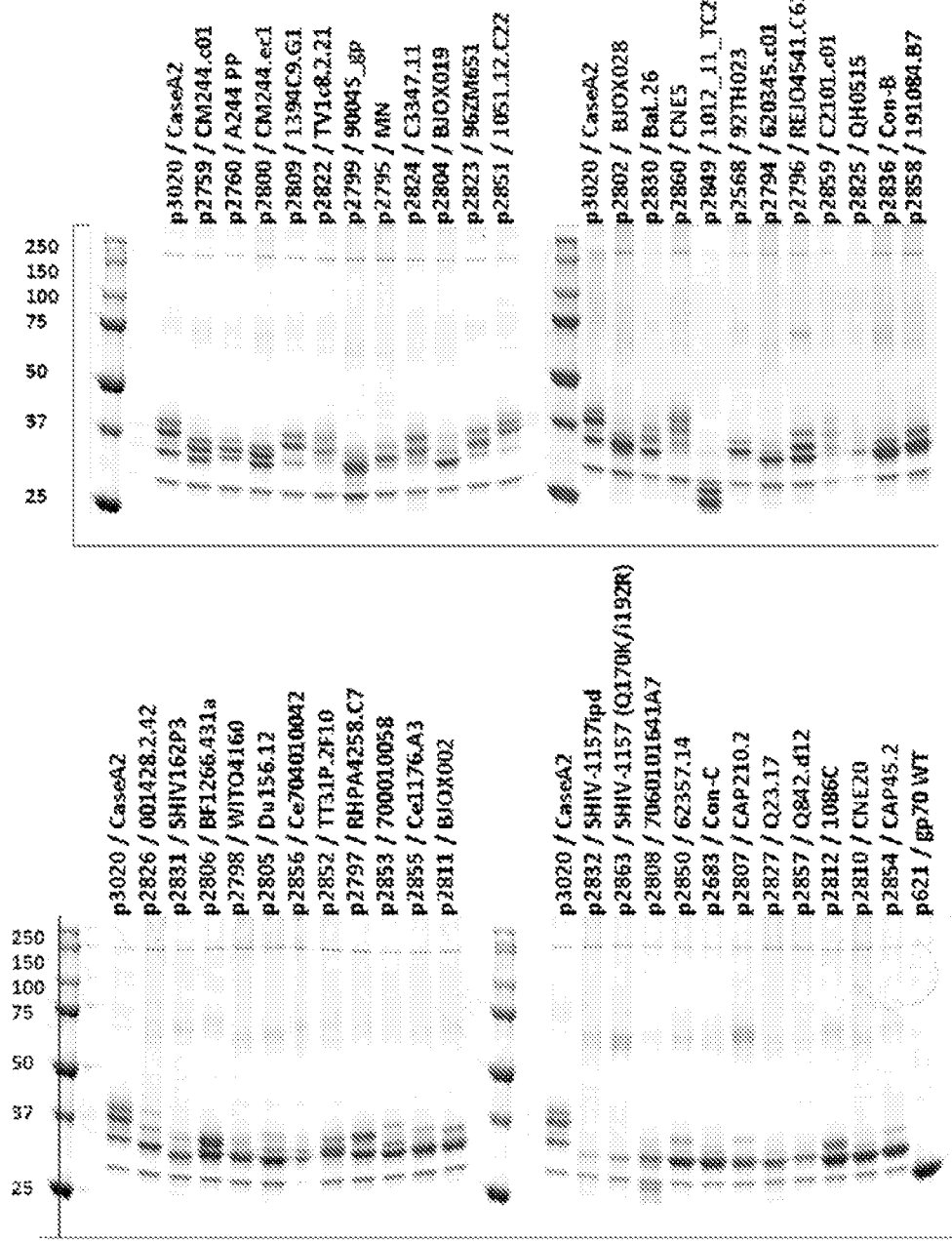

FIG. 12. Analysis of conformational heterogeneity in V1/V2 domain demonstrated by SDS-PAGE analysis of deglycosylated gp70-fusion proteins (+PngaseF, Non-Reduced). The plasmid number and sequence name are indicated above each sample. Samples are arranged according to the list in FIG. 11, according to size of the V1 hypervariable region. The CaseA2 sequence (p3020) is repeated in each gel to serve as a standard. Protein markers are also included as size standards. All samples were deglycosylated by treatment with PNGaseF before analysis. The data presented in this FIG. 12 represents gels run in unreduced form, while the bottom gels.

Figure 13:
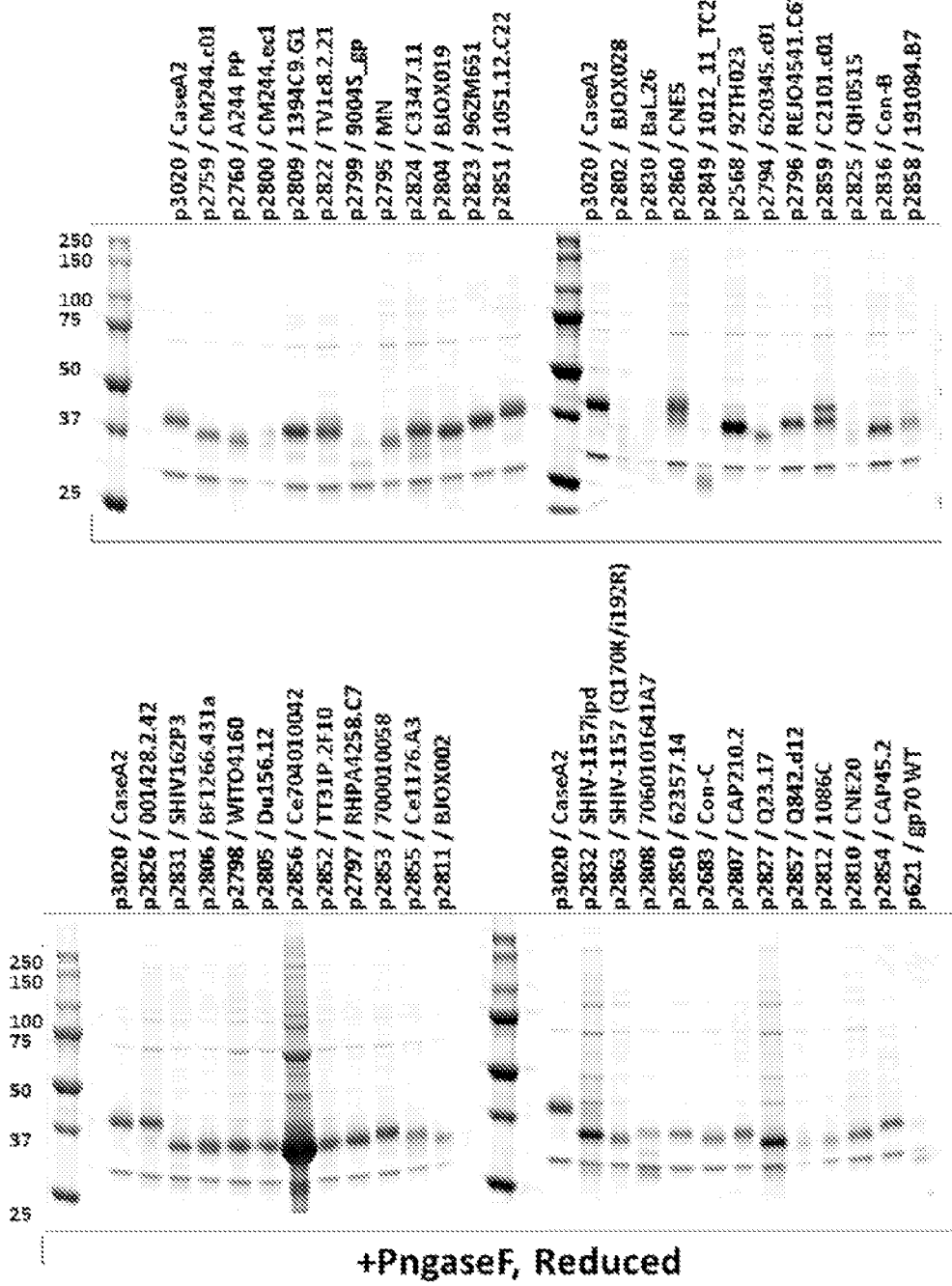

FIG. 13. Analysis of conformational heterogeneity in V1/V2 domain demonstrated by SDS-PAGE analysis of deglycosylated gp70-fusion proteins (+PngaseF, Reduced). See also, FIG. 12 legend. The data presented in this FIG. 13 represents the same samples analyzed as per FIG. 12, but after reduction of disulfide bonds by treatment with DTT.

FIG. 14. The CaseA2 gp70-V1/V2 sequence.

FIG. 15. The sequence of P565 plasmid.

DETAILED DESCRIPTION OF INVENTION

The present invention is based on the discovery that the V1/V2 domain of HIV Env-based antigens possesses conformational heterogeneity resulting from alternative disulfide bonding, which dramatically impacts the immunoreactivity of these proteins. In accordance with the present invention, the conformationally heterogenous antigens can be resolved to provide HIV Env antigens with homogeneous conformational forms of the V1/V2 domain.

Figure 2:
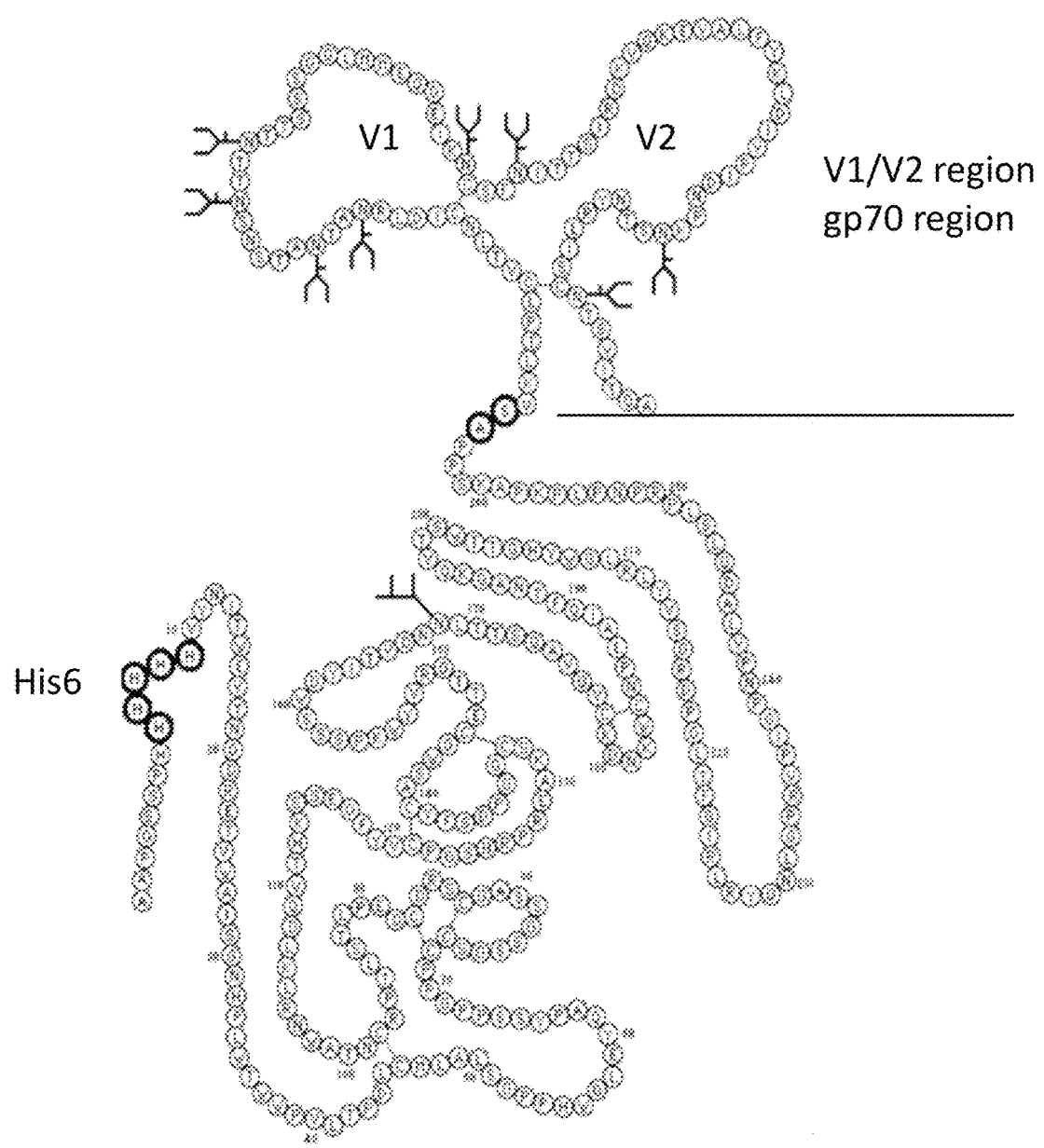

HIV envelope (Env) glycoproteins, including for example gp120 and p140, are known in the art and contain five constant and five variable domains. The V1/V2 domain comprises about 90 amino acids, including four cysteine residues designated herein as C1, C2, C3, and C4, with C1 being the most N-terminal and C4 being the most C-terminal. (FIGS. 2 6, and 7). The HIV Env antigens with homogeneous conformational forms of the V1/V2 domain provided herein are designated Form A, Form B, and Form C. In Form A, there is a disulfide bond between C1 and C4, and a disulfide bond between C2 and C3. In Form B, there is a disulfide bond between C1 and C3, and a disulfide bond between C2 and C4. In Form C, there is a disulfide bond between C1 and C2, and a disulfide bond between C3 and C4.

Forms A, B and C are present in native and recombinant HIV Env glycoproteins, and can be isolated from one another in accordance with the present invention. In particular, the present invention provides a method for isolating HIV Env antigens with Form A, or Form B, or Form C of the V1/V2 domain from each other to provide HIV Env antigens with a homogeneous conformational form of the V1/V2 domain. In particular, the different forms in a native or recombinant composition of HIV Env proteins can be separated from one another by immunoprecipitation with antibodies that are specific for the different conformations. For example, human Mab 8.22.2 (He et al., 2002, J. Immunol. 169:595-605) is specific for Form C. One of skill in the art can identify antibodies that are specific for the different conformations, and can perform immunoprecipitation, including serial immunoprecipitation, by methods known in the art to separate the different conformations. These forms can be fractionated by immunoaffinity methods using monoclonal antibodies that are specific for one of the distinct forms. The homogeneous forms may be obtained either in the depleted fraction or by elution of bound molecules.

Accordingly, in another embodiment, the present invention provides a composition of structurally and immunologically distinct HIV-1 antigens in which V1/V2 domains possess alternate disulfide bond patterns, i.e. Form A. Form B, or Form C, or combinations thereof, as disclosed herein. The antigens include at least the V1/V2 domain, and optionally other domains of the Env protein or other fusion partners. These antigens may consist of fusion glycoproteins that express the isolated V1/V2 domains as well as native gp120 and gp140 proteins that have been fractionated so that they contain homogeneously folded V1/V2 domains.

The antigens of the present invention are useful as antigens in immunoassays to characterize the specificity of antibodies directed against the V1/V2 domain in infected or immunized people. Accordingly, the invention further provides compositions comprising the antigens of the invention for use in such assays.

The antigens of the present invention are also useful as protein therapeutic agents for inhibiting functions mediated by the V1/V2 domain, and as immunogens in HIV vaccines. Accordingly, the present invention further provides pharmaceutical compositions comprising the antigens of the invention.

Formulations of the compositions useful in certain embodiments such as polypeptides, polynucleotides, or antibodies may be prepared for storage by mixing the selected composition having the desired degree of purity with optional physiologically pharmaceutically-acceptable carriers, excipients, or stabilizers (Remington's Pharmaceutical Sciences, 18th edition, A. R. Gennaro, ed., Mack Publishing Company (1990)) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Compositions to be used for in vivo administration should be sterile. This is readily accomplished by filtration through sterile filtration membranes, prior to or following lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle. The route of administration of the composition is in accord with known methods, e.g. oral, injection or infusion by intravenous, intraperitoneal, intracerebral, intramuscular, intraocular, intraarterial, or intralesional routes, or by sustained release systems or implantation device. Where desired, the compositions may be administered continuously by infusion, bolus injection or by implantation device.

An effective amount of the compositions to be employed therapeutically will depend, for example, upon the therapeutic objectives, the route of administration, and the condition of the patient. Accordingly, it may be necessary for the therapist to titer the dosage and modify the route of administration as required to obtain the optimal therapeutic effect. A typical daily dosage may range from about 1 g/kg to up to 100 mg/kg or more, depending on the factors mentioned above. Typically, a clinician will administer the composition until a dosage is reached that achieves the desired effect. The progress of this therapy is easily monitored by conventional assays designed to evaluate blood glucose levels or other particular conditions of interest in a particular subject.

Pharmaceutical compositions may be produced by admixing a pharmaceutically effective amount of protein with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

In certain embodiments, compounds are formulated with pharmaceutically acceptable diluents, adjuvants, excipients, or carriers. The phrase "pharmaceutically or pharmacologically acceptable" refers to molecular entities and compositions that do not produce adverse, allergic, or other untoward reactions when administered to an animal or a human, e.g., orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and/or surgical implantation at a particular site is contemplated as well.) Generally, this will also entail preparing compositions that are essentially free of pyrogens, as well as other impurities that could be harmful to humans or animals. The term "pharmaceutically acceptable carrier" includes any and all solvents, dispersion media, coatings, antibacterial and antifungal agents, isotonic and absorption delaying agents, liposomes, capsids, nanocapsules, microcapsules and the like. The use of such media and agents for pharmaceutically active substances is well known in the art.

The pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain embodiments, the present invention provides a method of treating a subject comprising administration of a composition. As used herein, the term "subject" is used to mean an animal, preferably a mammal, including a human. The terms "patient" and "subject" may be used interchangeably.

The therapeutic compositions may be administered by any route that delivers an effective dosage to the desired site of action, with acceptable (preferably minimal) side-effects. Numerous routes of administration of agents are known, for example, oral, rectal, transmucosal, or intestinal administration; parenteral delivery, including intramuscular, subcutaneous, intramedullary injections, as well as intrathecal, intraperitoneal, intranasal, cutaneous or intradermal injections; inhalation, and topical application.

Therapeutic dosing is achieved by monitoring therapeutic benefit and monitoring to avoid side-effects. Preferred dosage provides a maximum localized therapeutic benefit with minimum local or systemic side-effects. Suitable human dosage ranges for the polynucleotides or polypeptides can be extrapolated from these dosages or from similar studies in appropriate animal models. Dosages can then be adjusted as necessary by the clinician to provide maximal therapeutic benefit for human subjects.

When a therapeutically effective amount of a composition of the present invention is administered by e.g., intradermal, cutaneous or subcutaneous injection, the composition is preferably in the form of a pyrogen-free, parenterally acceptable aqueous solution. The preparation of such parenterally acceptable protein or polynucleotide solutions, having due regard to pH, isotonicity, stability, and the like, is within the skill in the art. A preferred composition should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the present invention may also contain stabilizers, preservatives, buffers, antioxidants, or other additives known to those of skill in the art. The agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The compositions of the invention may be in the form of a complex of the protein(s) or other active ingredient of present invention along with protein or peptide antigens.

The composition may further contain other agents which either enhance the activity of the protein or other active ingredient or complement its activity or use in treatment. Such additional factors and/or agents may be included in the pharmaceutical composition to produce a synergistic effect with protein or other active ingredient, or to minimize side effects.

Techniques for formulation and administration of the therapeutic compositions of the instant application may be found in "Remington's Pharmaceutical Sciences," Mack Publishing Co., Easton, Pa., latest edition. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

The antigens of the present invention are useful for identifying, for example by screening, and for generating antibodies or antigen-binding fragments thereof that are specific for antigens with homogeneous conformational forms of the V1/V2 domain.

Antibodies may take the form of any type of relevant antibody fragment, antibody binding portion, specific binding member, a non-protein synthetic mimic, or any other relevant terminology known in the art which refers to an entity which at least substantially retains the binding specificity/neutralization activity. Thus, the term "antibody" as used in any context within this specification is meant to include, but not be limited to, any specific binding member, immunoglobulin class and/or isotype (e.g., $IgG_1$, $IgG_2$, $IgG_3$, $IgG_4$, IgM, IgA, IgD, IgE and IgM); and biologically relevant fragment or specific binding member thereof, including but not limited to Fab, F(ab')2, Fv, and scFv (single chain or related entity). Therefore, it is well known in the art, and is included as review only, that an "antibody" refers to a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conversed while CDR regions (CDR1, CDR2 and CDR3) represent hypervariable regions and are arranged from NH.sub.2 terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors. That said, also included in the working definition of "antibody" are chimeric antibodies, humanized antibodies, a recombinant antibody, as human antibodies generated from a transgenic non-human animal, as well as antibodies selected from libraries using enrichment technologies available to the artisan. Antibody fragments are obtained using techniques readily known and available to those of ordinary skill in the art, as reviewed below. Therefore, an "antibody" is any such entity or specific binding member, which specifically binds the conformational epitope of the of the V1/V2 domain, as described herein. Therefore, the term "antibody" describes an immunoglobulin, whether natural or partly or wholly synthetically produced; any polypeptide or protein having a binding domain which is, or is substantially homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd and diabodies, as discussed without limitation, infra. It is known in the art that it is possible to manipulate monoclonal and other antibodies and use techniques of recombinant DNA technology to produce other antibodies or chimeric molecules which retain the specificity of the original antibody Such techniques may evolve introducing DNA encoding the immunoglobulin variable region, or the complementarity determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced. Antibodies can be modified in a number of ways, and the term "antibody" should be construed as covering any specific binding member or substance having a binding domain with the required specificity. Thus, this term covers antibody fragments, derivatives, functional equivalents and homologues of "antibody" including any polypeptide comprising an immunoglobulin binding domain, whether natural or wholly or partially synthetic. Such an entity may be a binding fragment encompassed within the term "antigen-binding portion" or "specific binding member" of an antibody including but not limited to (i) a Fab fragment, a monovalent fragment consisting of the VL, VH, CL and CH domains; (ii) a F(ab')2 fragment, a bivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody (v) a dAb fragment, which comprises a VH domain; (vi) an isolated complementarity determining region (CDR); (vii) a 'scAb', an antibody fragment containing VH and VL as well as either CL or CH; and (viii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application Publication No. WO 02/32925). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). In one embodiment, the invention provides a method for generating HIV-1 Env proteins with structurally homogeneous V1/V2 domains, and the use of such uniform structures as antigens, immunogens and therapeutic reagents.

Polyclonal or monoclonal antibodies for use in accordance with the present invention may be raised by known techniques. Monospecific murine (mouse) antibodies showing specificity to a conformational epitope of a target of choice may be purified from mammalian antisera containing antibodies reactive against this region, or may be prepared as monoclonal antibodies using the technique of Kohler and Milstein (1975, Nature 256: 495-497). Monospecific antibody as used herein is defined as a single antibody species or multiple antibody species with homogenous binding characteristics, such as the mouse monoclonal antibodies exemplified herein with the 13C3 series of monoclonal antibodies. Hybridoma cells are produced by mixing the splenic lymphocytes with an appropriate fusion partner, preferably myeloma cells, under conditions which will allow the formation of stable hybridomas. The splenic antibody producing cells and myeloma cells are fused, selected, and screened for antibody production. Hybridoma cells from antibody positive wells are cloned by a technique such as the soft agar technique of MacPherson (1973, Soft Agar Techniques, in Tissue Culture Methods and Applications, Kruse and Paterson, Eds, Academic Press). Monoclonal antibodies are produced in vivo by injecting respective hydridoma cells into pristine primed mice, collecting ascetic fluid after an interval of time, and prepared by techniques well known in the art.

Beyond species specific monoclonal antibodies described above, the antibodies of the present invention may also be in the form of a "chimeric antibody", a monoclonal antibody constructed from the variable regions derived from say, the murine source, and constant regions derived from the intended host source (e.g., human; for a review, see Morrison and Oi, 1989, Advances in Immunology, 44: 65-92). For example, the variable light and heavy DNA sequences from the rodent (e.g., mouse) antibody may be cloned into a mammalian expression vector. These light and heavy "chimeric" expression vectors are cotransfected into a recipient cell line and selected and expanded by known techniques. This cell line may then be subjected to known cell culture techniques, resulting in production of both the light chain and heavy chain of a chimeric antibody. Such chimeric antibodies have historically been shown to have the antigen-binding capacity of the original rodent monoclonal while significantly reducing immunogenicity problems upon host administration.

A logical improvement to the chimeric antibody is the "humanized antibody," which arguably reduces the chance of the patient mounting an immune response against a therapeutic antibody when compared to use of a chimeric or full murine monoclonal antibody The strategy of "humanizing" a murine Mab is based on replacing amino acid residues which differ from those in the human sequences by site directed mutagenesis of individual residues or by grafting of entire complementarity determining regions (Jones et al., 1986, Nature 321: 522-526). This technology is again now well known in the art and is represented by numerous strategies to improve on this technology; namely by implementing strategies including, but not limited to, "reshaping" (see Verhoeyen, et al., 1988, Science 239: 1534-1536), "hyperchimerization" (see Queen, et al., 1991, Proc. Natl. Acad. Sci. 88:2869-2873) or "veneering" (Mark, et al., 1994, Derivation of Therapeutically Active Humanized and Veneered anti-CD18 Antibodies Metcalf end Dalton, eds. Cellular Adhesion Molecular Definition to Therapeutic Potential. New York: Plenum Press, 291-312). These strategies all involve to some degree sequence comparison between rodent and human sequences to determine whether specific amino acid substitutions from a rodent to human consensus is appropriate. Whatever the variations, the central theme involved in generating a humanized antibody relies on CDR grafting, where these three antigen binding sites from both the light and heavy chain are effectively removed from the rodent expressing antibody clone and subcloned (or "grafted") into an expression vector coding for the framework region of the human antibody. For example, utilizing the above techniques a humanized antibody may be expressed wherein the CDR1, CDR2, and CDR3 regions of the variable light chain are prepared, and the CDR1, CDR2, and CDR3 regions of the variable heavy chain are prepared. Therefore, a "humanized antibody" is effectively an antibody constructed with only murine CDRs (minus any additional improvements generated by incorporating one or more of the above mentioned strategies), with the remainder of the variable region and all of the constant region being derived from a human source.

The invention also encompasses nucleic acid molecules encoding the proteins of the invention. Nucleic acid molecules within the invention can be cDNA, genomic DNA, synthetic DNA, or RNA, and can be double-stranded or single-stranded (i.e., either a sense or an antisense strand). Fragments of these molecules, which are also considered within the scope of the invention, can be produced, for example, by the polymerase chain reaction (PCR) or generated by treatment with one or more restriction endonucleases. A ribonucleic acid (RNA) molecule can be produced by in vitro transcription.

As used herein, both "protein" and "polypeptide" mean any chain of amino acid residues, regardless of length or post-translational modification (e.g., glycosylation or phosphorylation). The polypeptide can be a naturally occurring, synthetic, or a recombinant molecule consisting of a hybrid with one portion, for example, encoding all or a portion of a V1/V2 domain, and a second portion being encoded by all or part of a second gene.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

EXAMPLES

Example 1

Isolated V1/V2 Domain of HIV-1 Env Exists in at Least Two Structurally and Immunologically Distinct Forms The native V1/V2 domain of a clade B sequence (CaseA2) was expressed by fusion to the C-terminus of a 273 amino acid sequence fragment of the MuLV gp70 domain. This fusion glycoprotein was characterized by SDS-PAGE under various conditions, by radioimmunoprecipitation experiments with a panel of mAbs directed against V1/V2-specific epitopes, and by MALDI-TOF analysis of immunologically fractionated forms.

The CaseA2 gp70-V1/V2 sequence is set forth in FIG. 14. The sequence of P565 plasmid is set forth in FIG. 15. Plasmid has 1 HindIII site at the KL site in the V2 region

```
                                        (SEQ ID NO. 49)
CAG AAA GAA TAT GCA CTT TTT TAT AAG CTT GAT

ATA GTA CCA ATA GAT AAT (SEQ ID NO. 50)
Q K E Y A L F Y K L D I V P I D N
```

This can be mutated and a unique HindIII site can be inserted by silent mutations into the highly conserved KL site at the beginning of the V1 sequence

```
                                        (SEQ ID NO. 51)
CCC CCC GCT AGC GTA AAA TTA ACC CCA CTC (SEQ. ID NO. 52)
P P A S V K L T P L (SEQ ID NO. 6)
CCC CCC GCT AGC GTA A/Ag cTt ACC CCA CTC
                    HindIII
```

The V1/V2 domain of a number of HIV-1 Envs was expressed in isolated form as a disulfide-bonded glycoprotein joined to the C-terminus to a 273 amino acid fragment of the Friend MuLV gp70 protein. The CaseA2 V1/V2 fusion protein was radiolabeled and immunoprecipitated with monoclonal antibodies (mAbs) directed against a target in the gp70 carrier domain by capture of the antibody Fc regions with PANSORBIN®, a commercial preparation of crosslinked Staph A. The immunoprecipitated proteins were removed from PANSORBIN® by boiling in the presence of 1% SDS, and analyzed by SDS-PAGE before and after removal of all of the attached N-linked carbohydrate substituents both in non-reduced form and after reduction of disulfide bonds with dithiothreitol (DTT). Under non-reducing conditions a closely-spaced doublet was resolved on 10% gels at the position expected for the deglycosylated protein. These two bands coalesced into a single band with slightly lower mobility than the doublet after reduction, indicating that the doublet represented different disulfide-bonded conformeric forms. Analysis of samples immunoprecipitated with a variety of mAbs directed against sites in the V1/V2 domain contained either the upper or lower band, indicating that these represented two antigenically distinct conformeric forms. Analysis of the structure of the immunofractionated forms by MALDI-TOF mass spectrometry confirmed that these possessed distinct disulfide-bonded structures and allowed the assignment of the structures represented by the upper and lower band form.

These results demonstrate that the isolated V1/V2 domain of HIV-1 Env exists in at least two structurally and immunologically distinct forms.

Example 2

Heterogeneous Forms of V1/V2 Domains are not Limited to the Case-A2 Sequences

The biochemical method described above (SDS-PAGE of deglycosylated gp70-V1/V2 proteins under non-reducing conditions) allowed good resolution of structurally distinct V1/V2 forms of the Case-A2 sequence. However, applying the similar method to the BaL sequence resulted in a smaller separation between the two bands, and a modified SF162 sequence gave two bands that were barely distinguishable. Furthermore, for several other gp70-V1/V2 fusion proteins (e.g., the ConC sequence, or the Th023 clade A/E sequence) only a single band was observed. However, sequential immunoprecipitation assays revealed the presence of distinct conformational forms, indicating that the diverse forms were present, but could not be separated by gel electrophoresis.

Example 3

Direct Binding Studies with Rgp120/Rgp140 Proteins and Functional Studies

Evidence was also obtained for immunological heterogeneity in recombinant and native gp120 and gp140 immunogens. Sequential immunoprecipitations with monoclonal antibodies specific for distinct conformation epitopes in V1/V2 showed that these antibodies recognized only a fraction of the molecules (FIG. 1). Native and recombinant gp120 and gp140 proteins were recognized by MAbs specific for either the upper band-specific or lower band-specific epitopes, indicating the presence of both structures in these antigens. Finally, evidence has been presented that MAbs reactive with either upper band-specific or lower band-specific epitopes neutralized viral infectivity, indicating that both forms were present in functional Env proteins and suggesting that both contribute to viral binding and/or entry.

Analyses by sequential immunoprecipitations revealed that a substantial fraction (~25%) of three rgp120s tested were non-reactive with 697D, directed against a conformational V2 epitope. (FIG. 1A). C108g is a mAb isolated from an HIV-infected chimp that recognizes a glycan-dependent V1/V2 epitope overlapping with the PG9/PG16 site and possesses potent neutralizing activity against a limited set of viruses. C108g also recognized only a fraction of BaL rgp120 containing the correctly-folded V2 domain. (FIG. 1B).

Figure 3:
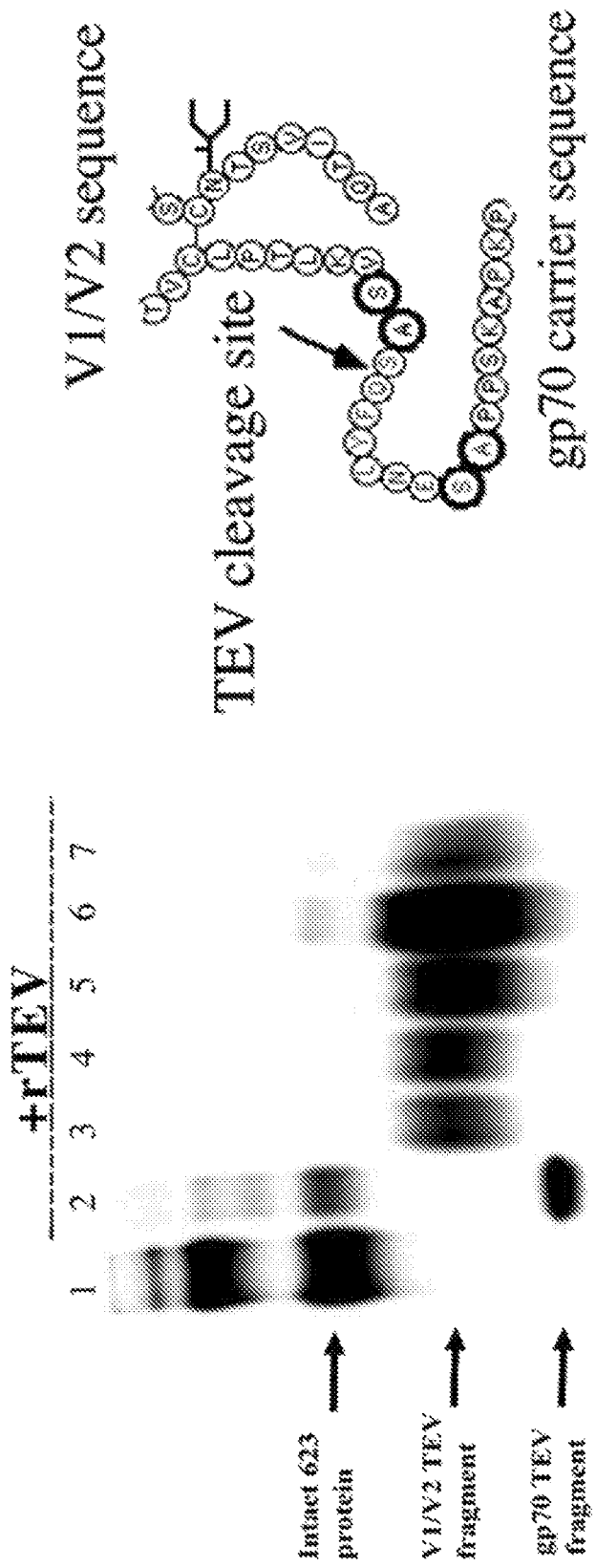
Figure 4:
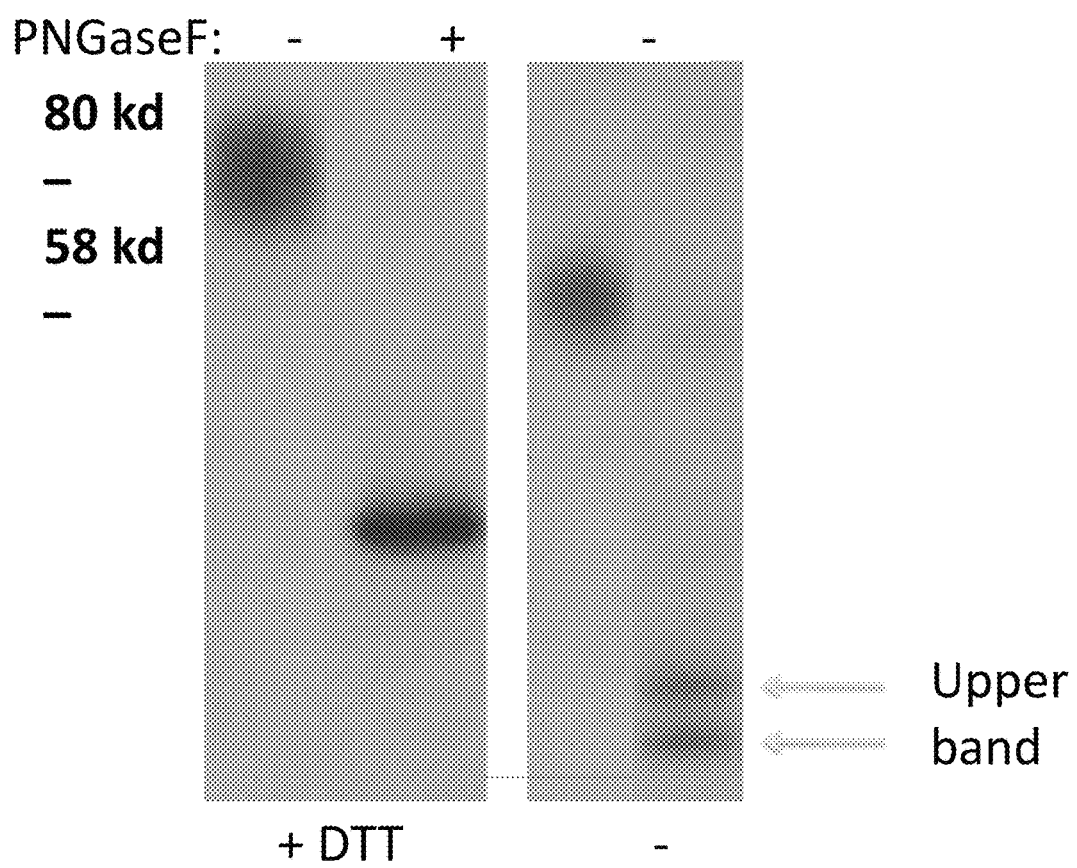
Figure 5:
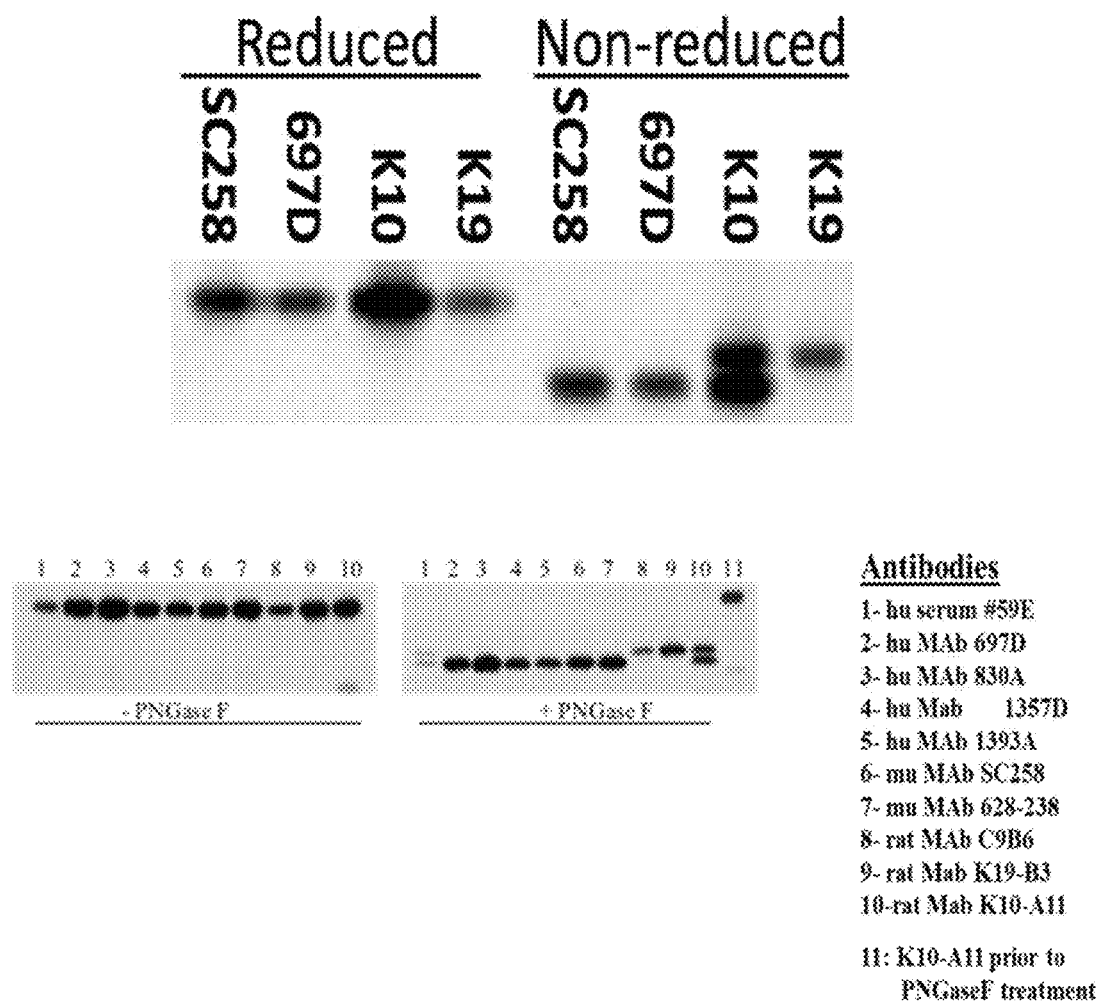

To facilitate the structural analysis of the native V1/V2 domain, this region of a primary clade B Env (CaseA2) sequence was expressed as a fusion protein, joined to an N-terminal fragment of the MuLV Env protein, gp70 (FIG. 2). This fusion protein system allowed the expression of the V1/V2 domain as a native glycosylated and disulfide-bonded protein. Separation of the V1/V2 domain from the gp70 domain by cleavage at a proteolytic site engineered between the two domains showed that these regions form distinct and independent folded domains (FIG. 3). The deglycosylated gp70-V1/V2$_{CaseA2}$ protein was resolved as a doublet by SDS-PAGE under non-reducing conditions, indicating distinct conformational forms (FIG. 4; see also FIG. 6 for three distinct and possible confirmations of the V1/V2 domain). The two V1/V2 conformational forms possess distinct immunoreactivities with V1V2-specific mAbs. Mabs isolated from infected humans and mice immunized with rgp120 all specifically recognize the V1/V2 lower band form. Mabs from rats immunized with V1/V2 fusion protein recognize upper band or both bands (FIG. 5).

Homogeneous conformational forms of the V1/V2 fusion protein were isolated by immunoaffinity chromatography and analyzed by mass spectrometry. The two forms were fractionated by immunoaffinity on columns containing lower band-specific mab 238. The flow-through contained upper band forms, while the column eluate contained the lower band form. The upper band form contained peptides at mass of 1573 and 2634 predicted for the C form, while the lower band form contained the complex peptide with mass of 4206 characteristic of forms A and B (FIG. 7).

Figure 8:
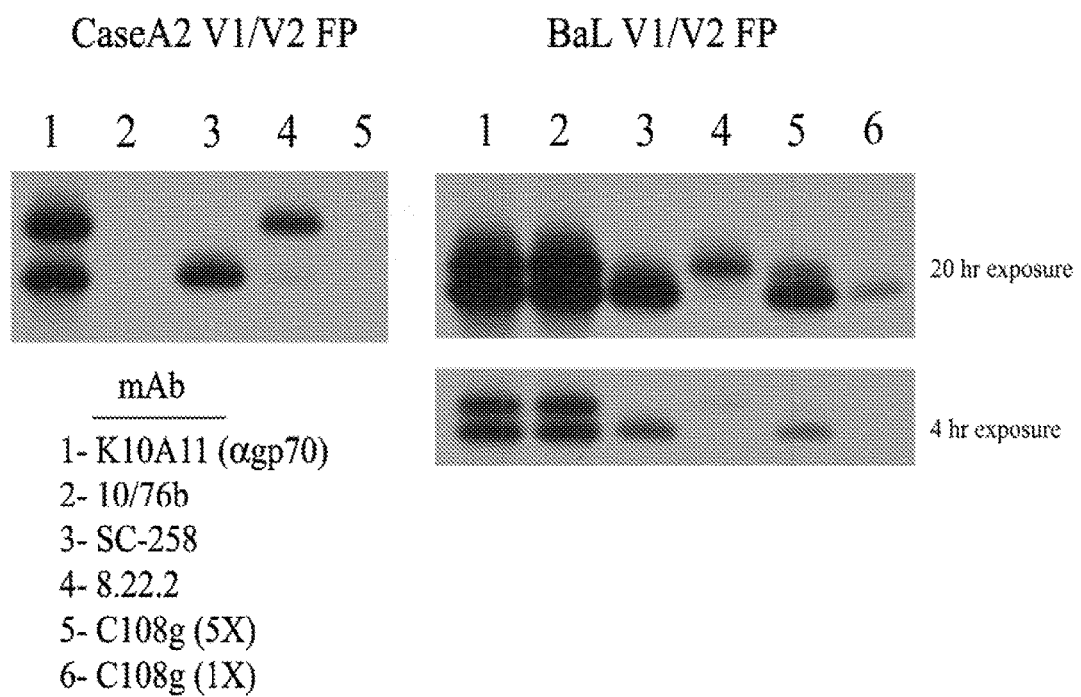

Alternate V1/V2 conformeric forms of the CaseA2 and BaL V1/V2 fusion proteins were analyzed (FIG. 8). For the CaseA2 protein, rat Mab K10A11 (directed against a site in the gp70 carrier domain) pulled down both forms; mouse Mab SC-258 recognized only lower form; and human Mab 8.22.2 (from immunized Xenomouse, which contained only human Ig genes) recognized predominantly upper band form. The two forms were also seen for BaL V1/V2 fusion protein, although they were not resolved as well. Again, K10A11 recognized both bands, rat Mab 10/76b, directed against a linear V2 epitope, recognized both upper and lower band equally well, while chimp Mab C108g recognized only the lower band form. The C108g epitope was not well-expressed in this protein, perhaps because of its glycan-dependence.

Figure 10:
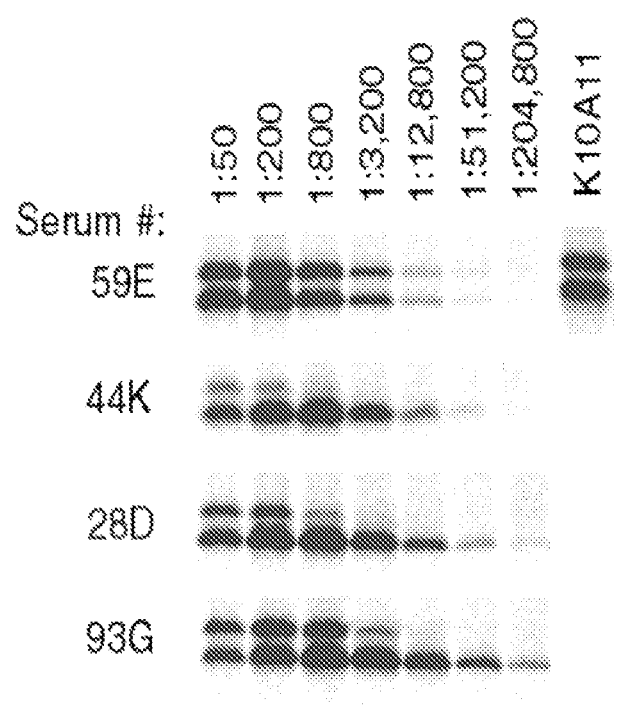

FIG. 9 shows an analysis of reactivity of human vaccine sera with conformers of the gp70-V1/V2$_{CaseA2}$ protein. Titrations of HIV-1-positive human immune sera show different patterns against specific V1/V2 conformers (FIG. 10).

The wide variety of various pg 120 V1/V2 sequence sequences exemplified herein are aligned in FIG. 11. The respective SEQ ID NO., plasmid number and corresponding names of Envs from which these sequences represent are provided within FIG. 11. The respective sequences are divided to indicate different regions of the V1/V2 domain; the conserved flanking regions, the V1 hypervariable region, the semi-conserved V2 region, the V2 hypervariable region and the V2 flank. It is also noted that these sequences are arranged by decreasing size of the V1 hypervariable region, and this order is reflected in the gels shown in both FIG. 12 ((+PngaseF, Non-Reduced)) and FIG. 13 ((+PngaseF, Reduced-DTT). FIGS. 12 and 13 show an analysis of the conformational heterogeneity in V1/V2 domain, as demonstrated by SDS-PAGE analysis of deglycosylated gp70-fusion proteins, in both non-reduced (FIG. 12) and reduced (FIG. 13) form. The plasmid number and sequence name are indicated above each sample in both FIG. 12 and FIG. 13. Samples are arranged according to the listing of FIG. 11, described above, as according to size of the V1 hypervariable region. The CaseA2 sequence (p3020) is repeated in each gel to serve as a standard. Protein markers are also included as size standards. All samples represented in both FIGS. 12 and 13 were deglycosylated by treatment with PNGaseF before analysis; again, with the gels of FIG. 12 being run in unreduced form and the gels of FIG. 13 representing gels showing samples analyzed after reduction of disulfide bonds by treatment with DTT. Many of the samples demonstrate multiple bands, similar in complexity to those seen for the CaseA2 protein. These bands coalesce to a single form after reduction (bottom gels). In general, samples with longer V1 hypervariable regions (left-hand gels) tend to display greated conformational diversity than samples with short V1 regions (right-hand gels).

INDUSTRIAL APPLICABILITY

The invention has applications in the treatment and diagnosis of HIV-1 virus infection disease. All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

---

What is claimed is:

1. An isolated and purified fusion polypeptide comprising an amino-terminal sequence directly linked to a V1/V2 domain of a HIV envelope protein having a structural configuration of a "C" form, a "B" form, or a "B"/"A" combined form and comprising amino acid residues 304-401 of SEQ ID NO:2.

2. The polypeptide of claim 1 wherein the HIV envelope protein has the sequence of a native gp120.

3. The polypeptide of claim 1 wherein the HIV envelope protein has the sequence of a native gp140.

4. The polypeptide of claim 1 wherein the HIV envelope protein is recombinant gp120.

5. The polypeptide of claim 1 wherein the HIV envelope protein is recombinant gp140.

6. The polypeptide of claim 4 wherein recombinant gp120 comprises a portion of the gp120 coding region, such that the antigenicity of the V1/V2 structural configuration of the "C" form, a "B" form, or a "B"/"A" combined form is maintained.

7. The polypeptide of claim 1, wherein the amino-terminal sequence represents a portion of MuLV gp70.

8. The polypeptide of claim 7 having the amino acid sequence of SEQ ID NO:2.

9. A method of inhibiting HIV replication in an HIV positive subject comprising administering to the subject a pharmaceutical composition comprising a polypeptide of claim 1, said pharmaceutical composition optionally containing a pharmaceutically active carrier, wherein administration of the pharmaceutical composition results in a reduction in HIV viral load.

10. A method of inducing neutralization of HIV viral infection in a human subject against infection or progression of HIV which comprises administration of a pharmaceutical composition which comprises a polypeptide of claim 1, said pharmaceutical composition optionally containing a pharmaceutically active carrier, wherein administration of the pharmaceutical composition results in generation of an immune response against HIV infection.

11. A pharmaceutical composition, comprising: (a) an effective amount of a polypeptide of claim 1; and, (b) optionally, a pharmaceutically acceptable carrier.

12. A method for inducing an enhanced immunological response against a HIV antigen in a mammalian host, said method comprising inoculating the mammalian host with a polypeptide of claim 1.

13. A method of identifying a HIV antiviral compound, comprising:

(a) combining component (i)—a test compound, component (ii)—a "C" form-specific, "B" form-specific, or "B"/"A" combined form-specific antibody, and component (iii)—a polypeptide of claim 1;

(b) measuring the effect the test compound has on the affinity of component (ii) for component (iii) of step (a); and, (c) comparing the effect the test compound has on the affinity of component (ii) for component (iii) versus the affinity of component (ii) for component (iii) in the absence of the test compound.

14. The method of claim 13 wherein component (i) is selected from the group consisting of a peptide, a protein, a non-proteinaceous organic or inorganic molecule, DNA and RNA.

* * * * *

SEQUENCE LISTING

<160> NUMBER OF SEQ ID NOS: 63

<210> SEQ ID NO 1
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1203)
<220> FEATURE:
<221> NAME/KEY: CDS
<222> LOCATION: (1219)..(1230)

<400> SEQUENCE: 1

```
atg gcg tgt tca acg ctc cca aaa tcc cct aaa gat aag att gac ccg        48
Met Ala Cys Ser Thr Leu Pro Lys Ser Pro Lys Asp Lys Ile Asp Pro
1               5                   10                  15 cgg gac ctc cta atc ccc tta att ctc ttc ctg tct ctc aaa ggg gcc        96
Arg Asp Leu Leu Ile Pro Leu Ile Leu Phe Leu Ser Leu Lys Gly Ala
                20                  25                  30 aga tcc gca gca ccc ggc tcc agc cct cac cat cac cac cat cac gtc       144
Arg Ser Ala Ala Pro Gly Ser Ser Pro His His His His His His Val
            35                  40                  45 tac aac att acc tgg gaa gtg acc aat ggg gat cgg gag aca gta tgg       192
Tyr Asn Ile Thr Trp Glu Val Thr Asn Gly Asp Arg Glu Thr Val Trp
        50                  55                  60 gca ata tca ggc aac cac cct ctg tgg act tgg tgg cca gtc ctc acc       240
Ala Ile Ser Gly Asn His Pro Leu Trp Thr Trp Trp Pro Val Leu Thr
65                  70                  75                  80 cca gat ttg tgt atg tta gct ctc agt ggg ccg ccc cac tgg ggg cta       288
Pro Asp Leu Cys Met Leu Ala Leu Ser Gly Pro Pro His Trp Gly Leu
                85                  90                  95 gag tat cag gcc ccc tat tcc tcg ccc ccg ggg ccc cct tgt tgc tca       336
Glu Tyr Gln Ala Pro Tyr Ser Ser Pro Pro Gly Pro Pro Cys Cys Ser
            100                 105                 110 ggg agc agc ggg agc agt gca ggc tgt tcc aga gac tgc gac gag ccc       384
Gly Ser Ser Gly Ser Ser Ala Gly Cys Ser Arg Asp Cys Asp Glu Pro
        115                 120                 125 ttg acc tcc ctc acc cct cgg tgc aac act gcc tgg aac aga ctt aag       432
Leu Thr Ser Leu Thr Pro Arg Cys Asn Thr Ala Trp Asn Arg Leu Lys
```

```
          130                 135                 140
cta gac cag gta act cat aaa tca agt gag gga ttt tat gtc tgc ccc      480
Leu Asp Gln Val Thr His Lys Ser Ser Glu Gly Phe Tyr Val Cys Pro
145                 150                 155                 160 ggg tca cat cgc ccc cgg gaa gcc aag tcc tgt gga ggt cca gac tcc      528
Gly Ser His Arg Pro Arg Glu Ala Lys Ser Cys Gly Gly Pro Asp Ser
                165                 170                 175 ttc tac tgt gcc tct tgg ggc tgc gag aca acc ggt aga gta tac tgg      576
Phe Tyr Cys Ala Ser Trp Gly Cys Glu Thr Thr Gly Arg Val Tyr Trp
            180                 185                 190 aag ccc tcc tcc tct tgg gac tac atc aca gtg gac aac aat ctc acc      624
Lys Pro Ser Ser Ser Trp Asp Tyr Ile Thr Val Asp Asn Asn Leu Thr
        195                 200                 205 act agc cag gct gtc cag gta tgc aaa gac aat aag tgg tgc aat ccc      672
Thr Ser Gln Ala Val Gln Val Cys Lys Asp Asn Lys Trp Cys Asn Pro
    210                 215                 220 ttg gct atc cag ttt aca aac gcc ggg aaa cag gtc acc tca tgg aca      720
Leu Ala Ile Gln Phe Thr Asn Ala Gly Lys Gln Val Thr Ser Trp Thr
225                 230                 235                 240 act gga cac tat tgg ggt cta cgt ctt tat gtc tct ggg cgg gac ccg      768
Thr Gly His Tyr Trp Gly Leu Arg Leu Tyr Val Ser Gly Arg Asp Pro
                245                 250                 255 ggg ctt act ttc ggg atc cga ctc aga tat caa aat cta gga cct cgg      816
Gly Leu Thr Phe Gly Ile Arg Leu Arg Tyr Gln Asn Leu Gly Pro Arg
            260                 265                 270 gtc ccg ata gga ccg aac ccc gtc ctg gca gac caa ctt tcg ctc ccg      864
Val Pro Ile Gly Pro Asn Pro Val Leu Ala Asp Gln Leu Ser Leu Pro
        275                 280                 285 cga cct aat ccc cta ccc aaa cct gcc aag tct ccc ccc gct agc gta      912
Arg Pro Asn Pro Leu Pro Lys Pro Ala Lys Ser Pro Pro Ala Ser Val
    290                 295                 300 aaa tta acc cca ctc tgt gtt act tta aat tgc att gat tta agg aat      960
Lys Leu Thr Pro Leu Cys Val Thr Leu Asn Cys Ile Asp Leu Arg Asn
305                 310                 315                 320 gct act aat gcc act agt aat agc aat act act aat acc act agt agt     1008
Ala Thr Asn Ala Thr Ser Asn Ser Asn Thr Thr Asn Thr Thr Ser Ser
                325                 330                 335 agc ggg gga ctg atg atg gaa caa gga gaa ata aaa aac tgc tct ttc     1056
Ser Gly Gly Leu Met Met Glu Gln Gly Glu Ile Lys Asn Cys Ser Phe
            340                 345                 350 aat atc acc aca agc ata aga gat aag gta cag aaa gaa tat gca ctt     1104
Asn Ile Thr Thr Ser Ile Arg Asp Lys Val Gln Lys Glu Tyr Ala Leu
        355                 360                 365 ttt tat aag ctt gat ata gta cca ata gat aat cct aaa aat agt acc     1152
Phe Tyr Lys Leu Asp Ile Val Pro Ile Asp Asn Pro Lys Asn Ser Thr
    370                 375                 380 aac tat agg ttg ata agt tgt aac acc tca gtc att aca cag gcc ggc     1200
Asn Tyr Arg Leu Ile Ser Cys Asn Thr Ser Val Ile Thr Gln Ala Gly
385                 390                 395                 400 gcc taatagatcg attag ttc aat ttg tta aa                             1232
Ala             Phe Asn Leu Leu
                            405

<210> SEQ ID NO 2
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 2

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His His His His His His Val
        35                  40                  45

Tyr Asn Ile Thr Trp Glu Val Thr Asn Gly Asp Arg Glu Thr Val Trp
    50                  55                  60

Ala Ile Ser Gly Asn His Pro Leu Trp Thr Trp Trp Pro Val Leu Thr
65                  70                  75                  80

Pro Asp Leu Cys Met Leu Ala Leu Ser Gly Pro Pro His Trp Gly Leu
                85                  90                  95

Glu Tyr Gln Ala Pro Tyr Ser Ser Pro Pro Gly Pro Pro Cys Cys Ser
            100                 105                 110

Gly Ser Ser Gly Ser Ser Ala Gly Cys Ser Arg Asp Cys Asp Glu Pro
        115                 120                 125

Leu Thr Ser Leu Thr Pro Arg Cys Asn Thr Ala Trp Asn Arg Leu Lys
    130                 135                 140

Leu Asp Gln Val Thr His Lys Ser Ser Glu Gly Phe Tyr Val Cys Pro
145                 150                 155                 160

Gly Ser His Arg Pro Arg Glu Ala Lys Ser Cys Gly Gly Pro Asp Ser
                165                 170                 175

Phe Tyr Cys Ala Ser Trp Gly Cys Glu Thr Thr Gly Arg Val Tyr Trp
            180                 185                 190

Lys Pro Ser Ser Ser Trp Asp Tyr Ile Thr Val Asp Asn Asn Leu Thr
        195                 200                 205

Thr Ser Gln Ala Val Gln Val Cys Lys Asp Asn Lys Trp Cys Asn Pro
    210                 215                 220

Leu Ala Ile Gln Phe Thr Asn Ala Gly Lys Gln Val Thr Ser Trp Thr
225                 230                 235                 240

Thr Gly His Tyr Trp Gly Leu Arg Leu Tyr Val Ser Gly Arg Asp Pro
                245                 250                 255

Gly Leu Thr Phe Gly Ile Arg Leu Arg Tyr Gln Asn Leu Gly Pro Arg
            260                 265                 270

Val Pro Ile Gly Pro Asn Pro Val Leu Ala Asp Gln Leu Ser Leu Pro
        275                 280                 285

Arg Pro Asn Pro Leu Pro Lys Pro Ala Lys Ser Pro Ala Ser Val
    290                 295                 300

Lys Leu Thr Pro Leu Cys Val Thr Leu Asn Cys Ile Asp Leu Arg Asn
305                 310                 315                 320

Ala Thr Asn Ala Thr Ser Asn Ser Asn Thr Thr Asn Thr Thr Ser Ser
                325                 330                 335

Ser Gly Gly Leu Met Met Glu Gln Gly Glu Ile Lys Asn Cys Ser Phe
            340                 345                 350

Asn Ile Thr Thr Ser Ile Arg Asp Lys Val Gln Lys Glu Tyr Ala Leu
        355                 360                 365

Phe Tyr Lys Leu Asp Ile Val Pro Ile Asp Asn Pro Lys Asn Ser Thr
    370                 375                 380

Asn Tyr Arg Leu Ile Ser Cys Asn Thr Ser Val Ile Thr Gln Ala Gly
385                 390                 395                 400

Ala
```

<210> SEQ ID NO 3
<211> LENGTH: 11256
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | | | | | |
|---|---|---|---|---|---|
| ttgggctgca | ggtcgatcga | ctctagaacc | caaaacgcgt | atttcggaca | aacacacccg | 60 |
| ctggaaagga | ccctataccg | tcctactgac | taccccacc | gctctcaaag | tagacggcat | 120 |
| tgcagcgtgg | atccacgctg | cccacgtaaa | ggctgccgac | accaggattg | agccaccagc | 180 |
| agaatcgaca | tggcgtgttc | aacgctccca | aaatcccta | aagataagat | tgacccgcgg | 240 |
| gacctcctaa | tccccttaat | tctcttcctg | tctctcaaag | gggccagatc | cgcagcaccc | 300 |
| ggctccagcc | ctcaccatca | ccaccatcac | gtctacaaca | ttacctggga | agtgaccaat | 360 |
| ggggatcggg | agacagtatg | gcaatatca | ggcaaccacc | ctctgtggac | ttggtggcca | 420 |
| gtcctcaccc | cagatttgtg | tatgttagct | ctcagtgggc | cgccccactg | ggggctagag | 480 |
| tatcaggccc | cctattcctc | gccccgggg | cccccttgtt | gctcagggag | cagcgggagc | 540 |
| agtgcaggct | gttccagaga | ctgcgacgag | cccttgacct | ccctcacccc | tcggtgcaac | 600 |
| actgcctgga | acagacttaa | gctagaccag | gtaactcata | aatcaagtga | gggattttat | 660 |
| gtctgccccg | ggtcacatcg | ccccgggaa | gccaagtcct | gtggaggtcc | agactccttc | 720 |
| tactgtgcct | cttggggctg | cgagacaacc | ggtagagtat | actggaagcc | ctcctcctct | 780 |
| tgggactaca | tcacagtgga | caacaatctc | accactagcc | aggctgtcca | ggtatgcaaa | 840 |
| gacaataagt | ggtgcaatcc | cttggctatc | cagtttacaa | acgccgggaa | acaggtcacc | 900 |
| tcatggacaa | ctggacacta | ttggggtcta | cgtctttatg | tctctgggcg | ggacccgggg | 960 |
| cttactttcg | ggatccgact | cagatatcaa | aatctaggac | ctcgggtccc | gataggaccg | 1020 |
| aaccccgtcc | tggcagacca | actttcgctc | ccgcgaccta | atccctacc | caaacctgcc | 1080 |
| aagtctcccc | ccgctagcgt | aaaattaacc | ccactctgtg | ttactttaaa | ttgcattgat | 1140 |
| ttaaggaatg | ctactaatgc | cactagtaat | agcaatacta | ctaataccac | tagtagtagc | 1200 |
| gggggactga | tgatggaaca | aggagaaata | aaaaactgct | ctttcaatat | caccacaagc | 1260 |
| ataagagata | aggtacagaa | agaatatgca | cttttttata | agcttgatat | agtaccaata | 1320 |
| gataatccta | aaaatagtac | caactatagg | ttgataagtt | gtaacacctc | agtcattaca | 1380 |
| caggccggcg | cctaatagat | cgattagttc | aatttgttaa | agacaggatc | tcagtagtcc | 1440 |
| aggctttagt | cctgactcaa | caataccacc | agctaaaacc | actagaatac | gagccatgat | 1500 |
| aaataaaaga | ttttatttag | tttccagaaa | aaggggggaa | tgaaagaccc | caccaagttg | 1560 |
| cttagggcga | gctcgaattc | attgatcata | atcagccata | ccacatttgt | agaggtttta | 1620 |
| cttgctttaa | aaaacctccc | acacctcccc | ctgaacctga | aacataaaat | gaatgcaatt | 1680 |
| gttgttgtta | acttgtttat | tgcagcttat | aatggttaca | aataaagcaa | tagcatcaca | 1740 |
| aatttcacaa | ataaagcatt | tttttcactg | cattctagtt | gtggtttgtc | caaactcatc | 1800 |
| aatgtatctt | atcatgtctg | gatcctctac | gccggacgca | tcgtggccgg | catcaccggc | 1860 |
| gccacaggtg | cggttgctgg | cgcctatatc | gccgacatca | ccgatgggga | agatcgggct | 1920 |
| cgccacttcg | ggctcatgag | cgcttgtttc | ggcgtgggta | tggtggcagg | ccccgtggcc | 1980 |
| gggggactgt | tgggcgccat | ctccttgcat | gcaccattcc | ttgcggcggc | ggtgctcaac | 2040 |

```
ggcctcaacc tactactggg ctgcttccta atgcaggagt cgcataaggg agagcgtcga   2100
cctcgggccg cgttgctggc gttttttccat aggctccgcc ccctgacga gcatcacaaa   2160 aatcgacgct caagtcagag gtggcgaaac ccgacaggac tataaagata ccaggcgttt   2220 cccctggaa gctccctcgt gcgctctcct gttccgaccc tgccgcttac cggatacctg    2280 tccgccttc tcccttcggg aagcgtggcg ctttctcata gctcacgctg taggtatctc    2340
agttcggtgt aggtcgttcg ctccaagctg ggctgtgtgc acgaaccccc cgttcagccc   2400
gaccgctgcg ccttatccgg taactatcgt cttgagtcca acccggtaag acacgactta   2460
tcgccactgg cagcagccac tggtaacagg attagcagag cgaggtatgt aggcggtgct   2520
acagagttct tgaagtggtg gcctaactac ggctacacta aaggacagt atttggtatc    2580 tgcgctctgc tgaagccagt taccttcgga aaaagagttg gtagctcttg atccggcaaa   2640
caaaccaccg ctggtagcgg tggtttttt gtttgcaagc agcagattac gcgcagaaaa    2700
aaaggatctc aagaagatcc tttgatcttt tctacggggt ctgacgctca gtggaacgaa   2760
aactcacgtt aagggatttt ggtcatgaga ttatcaaaaa ggatcttcac ctagatcctt    2820
ttaaattaaa aatgaagttt taaatcaatc taaagtatat atgagtaaac ttggtctgac    2880
agttaccaat gcttaatcag tgaggcacct atctcagcga tctgtctatt tcgttcatcc   2940
atagttgcct gactccccgt cgtgtagata actacgatac gggagggctt accatctggc   3000
cccagtgctg caatgatacc gcgagaccca cgctcaccgg ctccagattt atcagcaata   3060
aaccagccag ccggaagggc cgagcgcaga agtggtcctg caactttatc cgcctccatc   3120
cagtctatta attgttgccg ggaagctaga gtaagtagtt cgccagttaa tagttttcgc   3180
aacgttgttg ccattgctac aggcatcgtg gtgtcacgct cgtcgtttgg tatggcttca   3240
ttcagctccg gttcccaacg atcaaggcga gttacatgat cccccatgtt gtgcaaaaaa   3300
gcggttagct ccttcggtcc tccgatcgtt gtcagaagta agttggccgc agtgttatca   3360
ctcatggtta tggcagcact gcataattct cttactgtca tgccatccgt aagatgcttt   3420
tctgtgactg gtgagtactc aaccaagtca ttctgagaat agtgtatgcg gcgaccgagt   3480
tgctcttgcc cggcgtcaat acgggataat accgcgccac atagcagaac tttaaaagtg   3540
ctcatcattg gaaaacgttc ttcggggcga aaactctcaa ggatcttacc gctgttgaga   3600
tccagttcga tgtaacccac tcgtgcaccc aactgatctt cagcatcttt tactttcacc   3660
agcgtttctg ggtgagcaaa aacaggaagg caaaatgccg caaaaaaggg aataagggcg   3720
acacggaaat gttgaatact catactcttc ctttttcaat attattgaag catttatcag   3780
ggttattgtc tcatgagcgg atacatattt gaatgtattt agaaaaataa acaaataggg   3840
gttccgcgca catttccccg aaaagtgcca cctgacgtct aagaaaccat tattatcatg   3900
acattaacct ataaaaatag gcgtatcacg aggccctgat ggctctttgc ggcacccatc   3960
gttcgtaatg ttccgtggca ccgaggacaa ccctcaagag aaaatgtaat cacactggct   4020
caccttcggg tgggcctttc tgcgtttata aggagacact ttatgtttaa gaaggttggt   4080
aaattccttg cggctttggc agccaagcta gatccagctt tttgcaaaag cctaggcctc   4140
caaaaaagcc tcctcactac ttctggaata gctcagaggc cgaggcggcc tcggcctctg   4200
cataaataaa aaaaattagt cagccatggg gcggagaatg ggcggaactg gcggagtta    4260 ggggcgggat gggcggagtt aggggcggga ctatggttgc tgactaattg agatgcatgc   4320
tttgcatact tctgcctgct ggggagcctg ggactttcc acacctggtt gctgactaat    4380
tgagatgcat gctttgcata cttctgcctg ctggggagcc tggggacttt ccacaccccta   4440
```

```
actgacacac attccacagc caagctagct tgaattaatt cccgagccct tccaatacaa   4500
aaactaatta gactttgagt gatcttgagc ctttcctagt ttttgtattg gaagggctcg   4560
tcgccagtct cattgagaag gcatgtgcgg acgatggctt ctgtcactgc aaagggtca    4620 caattggcag aggggcggcg gtcttcaaag taacctttct tctcctggcc gagccgagaa   4680
tgggagtaga gccgactgct tgattcccac accaatctcc tcgccgctct cacttcgcct   4740
cgttctcgtg gctcgtggcc ctgtccaccc cgtccatcat cccgccggcc accgctcaga   4800
gcaccttcca ccatggccac ctcagcaagt tcccacttga acaaaaacat caagcaaatg   4860
tacttgtgcc tgccccaggg tgagaaagtc caagccatgt atatctgggt tgatggtact   4920
ggagaaggac tgcgctgcaa aacccgcacc ctggactgtg agcccaagtg tgtagaagag   4980
ttacctgagt ggaattttga tggctctagt acctttcagt ctgagggctc caacagtgac   5040
atgtatctca gccctgttgc catgtttcgg gaccccttcc gcagagatcc caacaagctg   5100
gtgttctgtg aagttttcaa gtacaaccgg aagcctgcag agaccaattt aaggcactcg   5160
tgtaaacgga taatggacat ggtgagcaac cagcacccct ggtttggaat ggaacaggag   5220
tatactctga tgggaacaga tgggcaccct tttggttggc cttccaatgg ctttcctggg   5280
ccccaaggtc cgtattactg tggtgtgggc gcagacaaag cctatggcag ggatatcgtg   5340
gaggctcact accgcgcctg cttgtatgct ggggtcaaga ttacaggaac aaatgctgag   5400
gtcatgcctg cccagtggga gttccaaata ggaccctgtg aaggaatccg catgggagat   5460
catctctggg tggcccgttt catcttgcat cgagtatgtg aagactttgg ggtaatagca   5520 accttttgacc ccaagcccat tcctgggaac tggaatggtg caggctgcca taccaacttt   5580
agcaccaagg ccatgcggga ggagaatggt ctgaagtaag tagcttcctc tggagccatc   5640
tttattctca tggggtggaa gggctttgtg ttagggttgg gaaagttgga cttctcacaa   5700
actacatgcc atgctcttcg tgtttgtcat aagcctatcg ttttgtaccc gttggagaag   5760
tgacagtact ctaggaatag aattacagct gtgatatggg aaagttgtca cgtaggttca   5820
agcatttaaa ggtctttagt aagaactaaa tacacataca agcaagtggg tgacttaatt   5880
cttactgatg ggaagaggcc agtgatgggg gtcttcccat ccaaaagata attggtatta   5940
catgttgagg actggtctga agcacttgag acataggtca caaggcagac acagcctgca   6000
tcaagtattt attggtttct tatggaactc atgcctgctc ctgcccttga aggacaggtt   6060
tctagtgaca aggtcagacc ctcacccttta ctgcttccac caggcacatc gaggaggcca   6120
tcgagaaact aagcaagcgg caccggtacc acattcgagc ctacgatccc aagggggcc    6180 tggacaatgc ccgtcgtctg actgggttcc acgaaacgtc caacatcaac gacttttctg   6240
ctggtgtcgc caatcgcagt gccagcatcc gcattcccg actgtcggc caggagaaga    6300 aaggttactt tgaagaccgc cgcccctctg ccaattgtga cccctttgca gtgacagaag   6360
ccatcgtccg cacatgcctt tcaatgaga ctggcgacga gccttccaa tacaaaaact    6420 aattagactt tgagtgatct tgagcctttc ctagttcatc ccaccccgcc ccagctgtct   6480
cattgtaact caaagtagtt catcccaccc cgccccagct gtctcattgt aactcaaagg   6540
gatggaatat caaggtcttt ttattcctcg tgcccagtta atcttgcttt tattggtcag   6600
aatagaggag tcaagttctt aatccctata cacccaaccc tcatttcttt tctatttagc   6660
tttctagtgg gggtgggagg ggtaggggaa gggaacgtaa ccactgcttc atctcatcag   6720
gaatgcatgt ccagtaggca gagctgccac agagtgggtg tatttgtgga ggaggacttt   6780
```

```
ttcttcagga cagttaaaag agcaggtcca ctgcttggat tgacaattcc cctataggta    6840
gagagctgct agttcttcag gtaaaaccaa ctttctattc caaatggaag ttaggtgagg    6900
agtagtggga ggagttcatg ccctccatga agacagctca gtgtatcacc tgacagatgg    6960
gtagccctac tgtaaaagaa ggaaaagtta tttctgggtc ctccatttat aacacaaagc    7020
agagtagtat ttttatattt aaatgtaaaa acaaaagtta tatatatgga tatgtggata    7080
tatgtgtatt tctaattgag gaaccatcc tagttactgg gtttgccaag tttgaagagc     7140
ttggttaaca agaaaggatc tcttgagtag aggtgggggt gcagtaccag gaaaggtggt    7200
tatctggggc tcagcgcttt attactatgt ggggtttccc tgcccactct gcaggagcag    7260
atgctggaca ggtagcaggg tgggacacca gtgctgccac cacctgtccc tgtgcttagg    7320
ctaagatgca tatgtatcca cacagagtta gcaggatgga gttggctggt caacttgaac    7380
attgttactg ataggggtgg gtggggttta ttttttggtg ggactagcat gtcactaaag    7440
caggcctttt gatatattaa attttttaaa gcaaaacaag ttcagctttt aatcaacttt    7500
gtagggtttc taactttaca gaattgcctg tttgtttcag tgtctccatc cactttgctc    7560
ttggaggaac ggaggacagg cagacctgga gttaaaacat ttgtcatttt gtgtcatagt    7620
gtctactttc tcccagcaga atattccttt ccttcttagg agtcctatgg agttttgttt    7680
ttgttttttt tctattacga taaacatacc ccacctccat tctggcttgc cctgctgttc    7740
tctggttgtt tgtgtgctgt ccgcagcagg ctgcctgtgg ttttctcttg ccatgacgac    7800
ttctaattgc catgtacagt atgttcagtt agataactcc tcattgtaaa cagactgtaa    7860
ctgccagagc agcgcttata aatcaaccta acatttataa gatttcctct tgacttgttt    7920
ctttgtggtt gggggaggaa gaaaaaaaaa agcgtgcagt attttttttgt tccttcattt    7980
cctatcaaaa gaaggggag tggttctgtt ttgtttactc gcaaaataag ctagcttatc     8040
tattggcttt tctttttttt tttttttta aacgggcttt ttcttgtacc tataatttgg     8100
ggtaaggtgt gagagttttt atagtttttt gagacagggt cttggtgtat acccttggct    8160
ggcctggagc taactatgta gactgggcta gcctttaact tgcagttctg ctttcaatta    8220
gggtttatac atttagtctt ggcaattcct agttccacgt ttaatctctt tacatttcaa    8280
agcagtgtta tctgaagagt tcaggcgcag agtcaattca atagagttac acaaaaacct    8340
aaaaaacaag ttttaaatac caagttatgt tggcctggcc acttttcaca gctgtccaca    8400
actcaatgtg acaaggctac aaattggata tactagaatt tcctggtgat ttggaacccc    8460
tgcttcattt cccggaacca gggcttttgg tgacagtcct agcttatcag attatttaaa    8520
acagttactc ttcctgccct tcttcctgag acctttgtcc agctgccatg agccatctac    8580
acagtacttg cttccctgtt gaagtcactg aaggcacatc agcccaagac ataaaggctt    8640
gtcccggatt cactagcctg gtgaacttgt ggttctctga tgttttgtcc tgttttgttg    8700
tgatttagtc tcaaatttcc cagcctggtt gaaaatctg ggctcccagc cttcaataag     8760
gaggactaca gatatgtacg actgagcctt gattccagcc tcatgtttat acgtctgtgc    8820
tcagctccct gaaggttcca gtttgaaact caataatcca ggggtcagaa agtcttgatc    8880
ttatccccac agtatggcac caagcctggc tgagccttct gacttagtct gccctgttgc    8940
tatttaagca cttttcttca ctaggctaaa aataaaagga gcttcctcct ttgccatggc    9000
gctgtgcatg ataggaaaag gtagctatct actagcatat taactccact gttttttgctt   9060
tgtgtgtttg gttttttgagg aagggtctca actgtgtatc cctggctggc ctggccggat    9120
ctagcttcgt gtcaaggacg gtgactgcag tgaataataa aatgtgtgtt tgtccgaaat    9180
```

```
acgcgttttg agatttctgt cgccgactaa attcatgtcg cgcgatagtg gtgtttatcg    9240
ccgatagaga tggcgatatt ggaaaaatcg atatttgaaa atatggcata ttgaaaatgt    9300
cgccgatgtg agtttctgtg taactgatat cgccattttt ccaaaagtga tttttgggca    9360
tacgcgatat ctggcgatag cgcttatatc gtttacgggg gatggcgata gacgactttg    9420
gtgacttggg cgattctgtg tgtcgcaaat atcgcagttt cgatataggt gacagacgat    9480
atgaggctat atcgccgata gaggcgacat caagctggca catggccaat gcatatcgat    9540
ctatacattg aatcaatatt ggccattagc catattattc attggttata tagcataaat    9600
caatattggc tattgccat tgcatacgtt gtatccatat cataatatgt acatttatat    9660
tggctcatgt ccaacattac cgccatgttg acattgatta ttgactagtt attaatagta    9720
atcaattacg gggtcattag ttcatagccc atatatggag ttccgcgtta cataacttac    9780
ggtaaatggc ccgcctggct gaccgcccaa cgaccccgc ccattgacgt caataatgac     9840
gtatgttccc atagtaacgc caatagggac tttccattga cgtcaatggg tggagtattt    9900
acggtaaact gcccacttgg cagtacatca agtgtatcat atgccaagta cgccccctat    9960
tgacgtcaat gacggtaaat ggcccgcctg gcattatgcc cagtacatga ccttatggga    10020
ctttcctact tggcagtaca tctacgtatt agtcatcgct attaccatgg tgatgcggtt    10080
ttggcagtac atcaatgggc gtggatagcg gtttgactca cggggatttc caagtctcca    10140
ccccattgac gtcaatggga gtttgttttg gcaccaaaat caacgggact ttccaaaatg    10200
tcgtaacaac tccgccccat tgacgcaaat gggcggtagg cgtgtacggt gggaggtcta    10260
tataagcaga gctcgtttag tgaaccgtca gatcgcctgg agacgccatc cacgctgttt    10320
tgacctccat agaagacacc gggaccgatc cagcctccgc ggccgggaac ggtgcattgg    10380
aacgcggatt ccccgtgcca agagtgacgt aagtaccgcc tatagagtct ataggcccac    10440
ccccttggct tcttatgcat gctatactgt ttttggcttg gggtctatac accccgctt     10500 cctcatgtta taggtgatgg tatagcttag cctataggtg tgggttattg accattattg    10560
accactcccc tattggtgac gatactttcc attactaatc cataacatgg ctctttgcca    10620
caactctctt tattggctat atgccaatac actgtccttc agagactgac acggactctg    10680
tatttttaca ggatggggtc tcatttatta tttacaaatt cacatataca acaccaccgt    10740
ccccagtgcc cgcagttttt attaaacata acgtgggatc tccacgcgaa tctcgggtac    10800
gtgttccgga catgggctct tctccggtag cggcggagct tctacatccg agccctgctc    10860
ccatgcctcc agcgactcat ggtcgctcgg cagctccttg ctcctaacag tggaggccaa    10920
acttaggcac agcacgatgc ccaccaccac cagtgtgccg cacaaggccg tggcggtagg    10980
gtatgtgtct gaaaatgagc tcggggagcg ggcttgcacc gctgacgcat ttggaagact    11040
taaggcagcg gcagaagaag atgcaggcag ctgagttgtt gtgttctgat aagagtcaga    11100
ggtaactccc gttgcggtgc tgttaacggt ggagggcagt gtagtctgag cagtactcgt    11160
tgctgccgcg cgcgccacca gacataatag ctgacagact aacagactgt tcctttccat    11220
gggtcttttc tgcagtcacc gtccttgaca cgaagc                             11256
```

<210> SEQ ID NO 4
<211> LENGTH: 1530
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(168)
<220> FEATURE:
<221> NAME/KEY: CDS
<222> LOCATION: (172)..(1392)
<220> FEATURE:
<221> NAME/KEY: CDS
<222> LOCATION: (1408)..(1434)
<220> FEATURE:
<221> NAME/KEY: CDS
<222> LOCATION: (1456)..(1473)
<220> FEATURE:
<221> NAME/KEY: CDS
<222> LOCATION: (1486)..(1503)
<220> FEATURE:
<221> NAME/KEY: CDS
<222> LOCATION: (1507)..(1530)

<400> SEQUENCE: 4

```
ttg ggc tgc agg tcg atc gac tct aga acc caa aac gcg tat ttc gga      48
Leu Gly Cys Arg Ser Ile Asp Ser Arg Thr Gln Asn Ala Tyr Phe Gly
1               5                   10                  15 caa aca cac ccg ctg gaa agg acc cta tac cgt cct act gac tac ccc      96
Gln Thr His Pro Leu Glu Arg Thr Leu Tyr Arg Pro Thr Asp Tyr Pro
            20                  25                  30 cac cgc tct caa agt aga cgg cat tgc agc gtg gat cca cgc tgc cca     144
His Arg Ser Gln Ser Arg Arg His Cys Ser Val Asp Pro Arg Cys Pro
        35                  40                  45 cgt aaa ggc tgc cga cac cag gat tga gcc acc agc aga atc gac atg     192
Arg Lys Gly Cys Arg His Gln Asp     Ala Thr Ser Arg Ile Asp Met
    50                  55                      60 gcg tgt tca acg ctc cca aaa tcc cct aaa gat aag att gac ccg cgg     240
Ala Cys Ser Thr Leu Pro Lys Ser Pro Lys Asp Lys Ile Asp Pro Arg
65                  70                  75 gac ctc cta atc ccc tta att ctc ttc ctg tct ctc aaa ggg gcc aga     288
Asp Leu Leu Ile Pro Leu Ile Leu Phe Leu Ser Leu Lys Gly Ala Arg
80                  85                  90                  95 tcc gca gca ccc ggc tcc agc cct cac cat cac cac cat cac gtc tac     336
Ser Ala Ala Pro Gly Ser Ser Pro His His His His His His Val Tyr
                100                 105                 110 aac att acc tgg gaa gtg acc aat ggg gat cgg gag aca gta tgg gca     384
Asn Ile Thr Trp Glu Val Thr Asn Gly Asp Arg Glu Thr Val Trp Ala
            115                 120                 125 ata tca ggc aac cac cct ctg tgg act tgg tgg cca gtc ctc acc cca     432
Ile Ser Gly Asn His Pro Leu Trp Thr Trp Trp Pro Val Leu Thr Pro
        130                 135                 140 gat ttg tgt atg tta gct ctc agt ggg ccg ccc cac tgg ggg cta gag     480
Asp Leu Cys Met Leu Ala Leu Ser Gly Pro Pro His Trp Gly Leu Glu
    145                 150                 155 tat cag gcc ccc tat tcc tcg ccc ccg ggg ccc cct tgt tgc tca ggg     528
Tyr Gln Ala Pro Tyr Ser Ser Pro Pro Gly Pro Pro Cys Cys Ser Gly
160                 165                 170                 175 agc agc ggg agc agt gca ggc tgt tcc aga gac tgc gac gag ccc ttg     576
Ser Ser Gly Ser Ser Ala Gly Cys Ser Arg Asp Cys Asp Glu Pro Leu
                180                 185                 190 acc tcc ctc acc cct cgg tgc aac act gcc tgg aac aga ctt aag cta     624
Thr Ser Leu Thr Pro Arg Cys Asn Thr Ala Trp Asn Arg Leu Lys Leu
            195                 200                 205 gac cag gta act cat aaa tca agt gag gga ttt tat gtc tgc ccc ggg     672
Asp Gln Val Thr His Lys Ser Ser Glu Gly Phe Tyr Val Cys Pro Gly
        210                 215                 220 tca cat cgc ccc cgg gaa gcc aag tcc tgt gga ggt cca gac tcc ttc     720
Ser His Arg Pro Arg Glu Ala Lys Ser Cys Gly Gly Pro Asp Ser Phe
```

```
              225                 230                 235
tac tgt gcc tct tgg ggc tgc gag aca acc ggt aga gta tac tgg aag    768
Tyr Cys Ala Ser Trp Gly Cys Glu Thr Thr Gly Arg Val Tyr Trp Lys
240                 245                 250                 255 ccc tcc tcc tct tgg gac tac atc aca gtg gac aac aat ctc acc act    816
Pro Ser Ser Ser Trp Asp Tyr Ile Thr Val Asp Asn Asn Leu Thr Thr
                260                 265                 270 agc cag gct gtc cag gta tgc aaa gac aat aag tgg tgc aat ccc ttg    864
Ser Gln Ala Val Gln Val Cys Lys Asp Asn Lys Trp Cys Asn Pro Leu
            275                 280                 285 gct atc cag ttt aca aac gcc ggg aaa cag gtc acc tca tgg aca act    912
Ala Ile Gln Phe Thr Asn Ala Gly Lys Gln Val Thr Ser Trp Thr Thr
        290                 295                 300 gga cac tat tgg ggt cta cgt ctt tat gtc tct ggg cgg gac ccg ggg    960
Gly His Tyr Trp Gly Leu Arg Leu Tyr Val Ser Gly Arg Asp Pro Gly
    305                 310                 315 ctt act ttc ggg atc cga ctc aga tat caa aat cta gga cct cgg gtc   1008
Leu Thr Phe Gly Ile Arg Leu Arg Tyr Gln Asn Leu Gly Pro Arg Val
320                 325                 330                 335 ccg ata gga ccg aac ccc gtc ctg gca gac caa ctt tcg ctc ccg cga   1056
Pro Ile Gly Pro Asn Pro Val Leu Ala Asp Gln Leu Ser Leu Pro Arg
                340                 345                 350 cct aat ccc cta ccc aaa cct gcc aag tct ccc ccc gct agc gta aaa   1104
Pro Asn Pro Leu Pro Lys Pro Ala Lys Ser Pro Pro Ala Ser Val Lys
            355                 360                 365 tta acc cca ctc tgt gtt act tta aat tgc att gat tta agg aat gct   1152
Leu Thr Pro Leu Cys Val Thr Leu Asn Cys Ile Asp Leu Arg Asn Ala
        370                 375                 380 act aat gcc act agt aat agc aat act act aat acc act agt agt agc   1200
Thr Asn Ala Thr Ser Asn Ser Asn Thr Thr Asn Thr Thr Ser Ser Ser
    385                 390                 395 ggg gga ctg atg atg gaa caa gga gaa ata aaa aac tgc tct ttc aat   1248
Gly Gly Leu Met Met Glu Gln Gly Glu Ile Lys Asn Cys Ser Phe Asn
400                 405                 410                 415 atc acc aca agc ata aga gat aag gta cag aaa gaa tat gca ctt ttt   1296
Ile Thr Thr Ser Ile Arg Asp Lys Val Gln Lys Glu Tyr Ala Leu Phe
                420                 425                 430 tat aag ctt gat ata gta cca ata gat aat cct aaa aat agt acc aac   1344
Tyr Lys Leu Asp Ile Val Pro Ile Asp Asn Pro Lys Asn Ser Thr Asn
            435                 440                 445 tat agg ttg ata agt tgt aac acc tca gtc att aca cag gcc ggc gcc   1392
Tyr Arg Leu Ile Ser Cys Asn Thr Ser Val Ile Thr Gln Ala Gly Ala
        450                 455                 460 taatagatcg attag ttc aat ttg tta aag aca gga tct cag tagtccagc    1444
                Phe Asn Leu Leu Lys Thr Gly Ser Gln
                465                 470 tttagtcctg a ctc aac aat acc acc agc taaaaccact ag aat acg agc    1494
             Leu Asn Asn Thr Thr Ser              Asn Thr Ser
                     475                                480 cat gat aaa taa aag att tta ttt agt ttc cag aaa                   1530
His Asp Lys     Lys Ile Leu Phe Ser Phe Gln Lys
                485                 490

<210> SEQ ID NO 5
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 5

```
Leu Gly Cys Arg Ser Ile Asp Ser Arg Thr Gln Asn Ala Tyr Phe Gly
1               5                   10                  15

Gln Thr His Pro Leu Glu Arg Thr Leu Tyr Arg Pro Thr Asp Tyr Pro
            20                  25                  30

His Arg Ser Gln Ser Arg Arg His Cys Ser Val Asp Pro Arg Cys Pro
        35                  40                  45

Arg Lys Gly Cys Arg His Gln Asp
    50                  55
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)

<400> SEQUENCE: 6

```
ccc ccc gct agc gta aag ctt acc cca ctc                           30
Pro Pro Ala Ser Val Lys Leu Thr Pro Leu
1               5                   10
```

<210> SEQ ID NO 7
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Ala Lys Leu Thr Pro Leu Cys Val Thr Leu Asn Cys Ile Asp Leu Arg
1               5                   10                  15

Asn Ala Thr Asn Ala Thr Ser Asn Ser Asn Thr Thr Asn Thr Thr Ser
            20                  25                  30

Ser Ser Gly Gly Leu Met Met Glu Gln Gly Glu Ile Lys Asn Cys Ser
        35                  40                  45

Phe Asn Ile Thr Thr Ser Ile Arg Asp Lys Val Gln Lys Glu Tyr Ala
    50                  55                  60

Leu Phe Tyr Lys Leu Asp Ile Val Pro Ile Asp Asn Pro Lys Asn Ser
65                  70                  75                  80

Thr Asn Tyr Arg Leu Ile Ser Cys Asn Thr Ser Val Ile Thr Gln Ala
                85                  90                  95
```

<210> SEQ ID NO 8
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Val Lys Leu Thr Pro Leu Cys Val Thr Leu His Cys Thr Asn Ala Asn
1               5                   10                  15

Leu Thr Lys Ala Asn Leu Thr Asn Val Asn Asn Arg Thr Asn Val Ser
            20                  25                  30

Asn Ile Ile Gly Asn Ile Thr Asp Glu Val Arg Asn Cys Ser Phe Asn
```

```
                35                  40                  45
Met Thr Thr Glu Leu Arg Asp Lys Lys Gln Lys Val His Ala Leu Phe
            50                  55                  60

Tyr Lys Leu Asp Ile Val Pro Ile Glu Asp Asn Asn Asp Ser Ser Glu
65                  70                  75                  80

Tyr Arg Leu Ile Asn Cys Asn Thr Ser Val Ile Lys Gln Ala
                85                  90

<210> SEQ ID NO 9
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Lys Leu Thr Pro Pro Cys Val Thr Leu His Cys Thr Asn Ala Asn
1               5                   10                  15

Leu Thr Lys Ala Asn Leu Thr Asn Val Asn Asn Arg Thr Asn Val Ser
                20                  25                  30

Asn Ile Ile Gly Asn Ile Thr Asp Glu Val Arg Asn Cys Ser Phe Asn
            35                  40                  45

Met Thr Thr Glu Leu Arg Asp Lys Lys Gln Lys Val His Ala Leu Phe
            50                  55                  60

Tyr Lys Leu Asp Ile Val Pro Ile Glu Asp Asn Asn Asp Ser Ser Glu
65                  70                  75                  80

Tyr Arg Leu Ile Asn Cys Asn Thr Ser Val Ile Lys Gln Pro
                85                  90

<210> SEQ ID NO 10
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Lys Leu Thr Pro Leu Cys Val Thr Leu His Cys Thr Asn Ala Asn
1               5                   10                  15

Leu Thr Lys Ala Asn Leu Thr Asn Val Asn Asn Arg Thr Asn Val Ser
                20                  25                  30

Asn Ile Ile Gly Asn Ile Thr Asp Glu Val Arg Asn Cys Ser Phe Asn
            35                  40                  45

Met Thr Thr Glu Leu Arg Asp Lys Lys Gln Lys Val His Ala Leu Phe
            50                  55                  60

Tyr Lys Leu Asp Ile Val Pro Ile Glu Asp Asn Asn Asp Asn Ser Lys
65                  70                  75                  80

Tyr Arg Leu Ile Asn Cys Asn Thr Ser Val Ile Lys Gln Ala
                85                  90

<210> SEQ ID NO 11
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

```
Val Lys Leu Thr Pro Leu Cys Val Thr Leu Glu Cys Thr Asn Val Thr
1               5                   10                  15

Leu Lys Asp Thr Asn Gly Asn Ser Thr Ser Gly Asn Asp Thr Asn Val
            20                  25                  30

Asp Asn Glu Lys Ala Ile Asn Glu Asp Met Arg Asn Cys Ser Phe Asn
        35                  40                  45

Val Thr Thr Val Val Arg Asp Lys Lys Lys Glu Asn Ala Leu Phe
    50                  55                  60

Tyr Lys Val Asp Ile Val Pro Leu Phe Gly Asp Asn Ser Ser Met Tyr
65                  70                  75                  80

Arg Leu Ile Asn Cys Asn Thr Ser Thr Ile Thr Gln Ala
                85                  90
```

<210> SEQ ID NO 12
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Val Lys Leu Thr Pro Leu Cys Val Thr Leu Asn Cys Thr Glu Thr Asn
1               5                   10                  15

Val Thr Gly Asn Arg Thr Val Ile Gly Asn Thr Asn Asp Thr Asn Ile
            20                  25                  30

Ala Asn Ala Thr Tyr Lys Tyr Glu Glu Met Lys Asn Cys Ser Phe Asn
        35                  40                  45

Val Thr Thr Glu Leu Arg Asn Lys Lys His Lys Glu Tyr Ala Leu Phe
    50                  55                  60

Tyr Arg Leu Asp Ile Val Pro Leu Asn Glu Asn Gly Asp Asn Ser Lys
65                  70                  75                  80

Tyr Arg Leu Ile Asn Cys Asn Thr Ser Ala Ile Thr Gln Ala
                85                  90
```

<210> SEQ ID NO 13
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Val Lys Leu Thr Pro Leu Cys Val Thr Leu Asn Cys Ser Gln Tyr Val
1               5                   10                  15

Ser Ser His Val Asn Asn His Asn Ser Ser His Asn Val Ser Ser
            20                  25                  30

His Ser Gly Asn Ile Thr Ser Asp Met Lys Ile Cys Ser Phe Asn Thr
        35                  40                  45

Thr Thr Glu Val Arg Asp Lys Lys Gln Lys Val Tyr Ser Leu Phe Tyr
    50                  55                  60

Lys Leu Asp Val Val Pro Ile Ser Asn Asp Ser Ser Gln Tyr Arg Leu
65                  70                  75                  80

Ile Asn Cys Asn Thr Ser Ala Ile Thr Gln Ala
                85                  90
```

<210> SEQ ID NO 14

<211> LENGTH: 91
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 14

Val Lys Leu Thr Pro Leu Cys Val Thr Leu Asn Cys Thr Asp Leu Arg
1               5                   10                  15

Asn Thr Thr Asn Thr Asn Asn Asn Thr Asp Asn Asn Ser Lys Ser
            20                  25                  30

Glu Gly Thr Ile Lys Gly Gly Glu Met Lys Asn Cys Ser Phe Asn Ile
        35                  40                  45

Thr Thr Ser Ile Gly Asp Lys Met Gln Lys Glu Tyr Ala Leu Leu Tyr
    50                  55                  60

Lys Leu Asp Ile Val Ser Ile Asp Asn Asp Ser Thr Ser Tyr Arg Leu
65                  70                  75                  80

Ile Ser Cys Asn Thr Ser Val Ile Thr Gln Ala
                85                  90

<210> SEQ ID NO 15
<211> LENGTH: 97
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 15

Val Lys Leu Thr Pro Leu Cys Val Thr Leu Asn Cys Thr Asp Val Asn
1               5                   10                  15

Thr Asn Gly Thr Thr Asn Thr Thr Ala Thr Thr Thr Asn Ser Ser Gly
            20                  25                  30

Glu Ile Glu Glu Lys Gly Glu Ile Lys Asn Cys Ser Phe Asn Val Thr
        35                  40                  45

Ser Gly Ile Arg Asp Lys Met Gln Lys Glu Tyr Ala Phe Phe Tyr Lys
    50                  55                  60

Leu Asp Val Val Pro Ile Asp Asn His Ser Asn Asn Asp Ser Ser Ser
65                  70                  75                  80

Tyr Arg Ser Tyr Arg Met Ile Ser Cys Asn Thr Ser Val Ile Thr Gln
                85                  90                  95

Ala

<210> SEQ ID NO 16
<211> LENGTH: 93
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 16

Val Lys Leu Thr Pro Leu Cys Val Thr Leu Asn Cys Thr Lys Ala Asn
1               5                   10                  15

Leu Thr Ser Asp Thr Thr Asn Arg Thr Thr Gly Asn Arg Ile Asp Glu
            20                  25                  30

Val Gly Asn Met Thr Asp Glu Val Lys Asn Cys Thr Phe Asn Met Thr
        35                  40                  45

Thr Glu Leu Lys Asp Lys Lys Gln Lys Val His Ala Leu Phe Tyr Lys

Leu Asp Ile Val Pro Ile Lys Gly Asn Glu Asn Ser Ser Gly Glu Tyr
65                  70                  75                  80

Arg Leu Ile Asn Cys Asn Thr Ser Val Ile Lys Gln Ala
                85                  90

<210> SEQ ID NO 17
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Val Lys Leu Thr Pro Leu Cys Val Thr Leu Asn Cys Thr Asn Val Asn
1               5                   10                  15

Ser Asn Ser Ser Ser Asn Ser Ser Asn Ser Ser Gly Asn Ser Asn Ser
                20                  25                  30

Thr Phe Glu Asn Met Gln Glu Met Lys Asn Cys Ser Phe Asn Thr Thr
            35                  40                  45

Thr Glu Leu Arg Asp Lys Lys Gln Lys Val Tyr Ala Leu Phe Tyr Arg
    50                  55                  60

Leu Asp Ile Val Pro Leu Ser Glu Asn Ser Ser Glu Tyr Arg Leu Ile
65                  70                  75                  80

Asn Cys Asn Thr Ser Ala Ile Thr Gln Ala
                85                  90

<210> SEQ ID NO 18
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Val Lys Leu Thr Pro Leu Cys Val Thr Leu Asn Cys Thr Glu Val Asn
1               5                   10                  15

Val Thr Arg Asn Val Asn Asn Ser Val Val Asn Asn Thr Thr Asn Val
                20                  25                  30

Asn Asn Ser Met Asn Gly Asp Met Lys Asn Cys Ser Phe Asn Ile Thr
            35                  40                  45

Thr Glu Leu Lys Asp Lys Lys Lys Asn Val Tyr Ala Leu Phe Tyr Lys
    50                  55                  60

Leu Asp Ile Val Ser Leu Asn Glu Thr Asp Ser Glu Thr Gly Asn
65                  70                  75                  80

Ser Ser Lys Tyr Tyr Arg Leu Ile Asn Cys Asn Thr Ser Ala Leu Thr
                85                  90                  95

Gln Ala

<210> SEQ ID NO 19
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Ala Lys Leu Thr Pro Leu Cys Val Thr Leu Asn Cys Thr Asp Leu Lys
1               5                   10                  15

Asn Ala Thr Asn Gly Asn Thr Asn Thr Thr Ser Ser Ser Gly Gly
            20                  25                  30

Met Met Gly Gly Gly Glu Met Lys Asn Cys Ser Phe Asn Ile Thr Thr
            35                  40                  45

Asn Ile Arg Gly Lys Val Gln Lys Glu Tyr Ala Leu Phe Tyr Glu Leu
50                  55                  60

Asp Ile Val Pro Ile Asp Asn Lys Ile Asp Ser Tyr Arg Leu Ile Ser
65                  70                  75                  80

Cys Asn Thr Ser Val Ile Thr Gln Ala
                85

<210> SEQ ID NO 20
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Lys Leu Thr Pro Leu Cys Val Thr Leu Asn Cys Ser Asn Ala Glu
1               5                   10                  15

Leu Thr Asn Leu Thr Asn Phe Asn Lys Thr Asn Val Phe Lys Gly Ile
            20                  25                  30

Gly Asn Val Thr Asp Glu Val Arg Asn Cys Ser Phe Asn Met Thr Thr
            35                  40                  45

Leu Leu Thr Asp Lys Lys Gln Met Val His Ala Leu Phe Tyr Lys Leu
50                  55                  60

Asp Ile Ile Gln Ile Ser Asn Ser Ser Tyr Arg Leu Ile Asn Cys Asn
65                  70                  75                  80

Thr Ser Val Ile Lys Gln Ala
                85

<210> SEQ ID NO 21
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Lys Leu Thr Pro Leu Cys Val Thr Leu Asn Cys Thr Asp Val Thr
1               5                   10                  15

Asn Ala Thr Asn Ile Asn Ala Thr Asn Ile Asn Ser Ser Gly Gly
            20                  25                  30

Val Glu Ser Gly Glu Ile Lys Asn Cys Ser Phe Asn Ile Thr Thr Ser
            35                  40                  45

Val Arg Asp Lys Val Gln Lys Glu Tyr Ala Leu Phe Tyr Lys Leu Asp
50                  55                  60

Ile Val Pro Ile Thr Asn Glu Ser Ser Lys Tyr Arg Leu Ile Ser Cys
65                  70                  75                  80

Asn Thr Ser Val Leu Thr Gln Ala
                85

<210> SEQ ID NO 22
<211> LENGTH: 91
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Lys Leu Thr Pro Leu Cys Val Thr Leu His Cys Thr Thr Leu Asn
1               5                   10                  15

Ile Thr Asn Thr Thr Arg Asn Val Thr Thr Pro Gly Pro Asn Leu Gly
            20                  25                  30

Asn Ile Thr Asp Glu Val Arg Asn Cys Ser Phe Asn Val Thr Thr Glu
        35                  40                  45

Ile Arg Asp Lys Lys His Lys Val Asn Ala Leu Phe Tyr Lys Leu Asp
50                  55                  60

Ile Val Gln Ile Glu Asn Asn Asn Asn Ser Asn Lys Tyr Arg Leu
65                  70                  75                  80

Ile Asn Cys Asn Thr Ser Val Ile Lys Gln Ala
            85                  90

<210> SEQ ID NO 23
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Lys Leu Thr Pro Leu Cys Val Thr Leu Asn Cys Thr Asn Ala Asn
1               5                   10                  15

Val Thr Asn Val Lys Asn Ile Thr Asn Val Pro Asn Ile Ile Gly Asn
            20                  25                  30

Ile Thr Asp Glu Val Arg Asn Cys Ser Phe Asn Met Thr Thr Glu Leu
        35                  40                  45

Arg Asp Lys Lys Gln Lys Val His Ala Leu Phe Tyr Lys Leu Asp Ile
50                  55                  60

Val Pro Ile Glu Asp Asn Thr Ser Ser Ser Glu Tyr Arg Leu Ile Asn
65                  70                  75                  80

Cys Asn Thr Ser Val Ile Lys Gln Ala
            85

<210> SEQ ID NO 24
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ile Lys Leu Thr Pro Leu Cys Val Thr Leu Ser Cys Thr Glu Ala Lys
1               5                   10                  15

Phe Asn Glu Thr Phe Asn Lys Ile Asp Asn Ile Thr Lys Val Ser Asn
            20                  25                  30

Leu Thr Asp Glu Met Arg Asn Cys Ser Phe Asn Met Thr Thr Glu Leu
        35                  40                  45

Arg Asp Lys Lys Gln Gln Val Tyr Ala Leu Phe Tyr Lys Leu Asp Ile
50                  55                  60

Val Pro Ile Asp Asn Ser Ser Glu Tyr Arg Leu Ile Asn Cys Asn Thr
```

65                  70                  75                  80

Ser Val Ile Lys Gln Ala
                85

<210> SEQ ID NO 25
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Val Lys Leu Thr Pro Leu Cys Val Thr Leu Lys Cys Thr Asp Leu Asn
1               5                   10                  15

Val Thr Asn Ser Asn Ser Thr Asp His Ser Thr Asn Ser Ser Leu Glu
            20                  25                  30

Ala Lys Gly Glu Ile Lys Asn Cys Ser Phe Asn Ile Thr Thr Thr Pro
        35                  40                  45

Arg Asp Lys Ile Gln Lys Glu Tyr Ala Ile Phe Tyr Lys Gln Asp Val
    50                  55                  60

Val Pro Ile Lys Asn Asp Asn Ile Ser Tyr Arg Leu Ile Ser Cys Asn
65                  70                  75                  80

Thr Ser Val Ile Thr Gln Ala
                85

<210> SEQ ID NO 26
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Val Lys Leu Thr Pro Leu Cys Val Thr Leu Asn Cys Thr Asp Lys Leu
1               5                   10                  15

Arg Asn Asp Thr Ser Gly Thr Asn Ser Ser Ser Trp Glu Lys Val Gln
            20                  25                  30

Lys Gly Glu Ile Lys Asn Cys Ser Phe Asn Ile Thr Thr Gly Ile Arg
        35                  40                  45

Gly Arg Val Gln Glu Tyr Ser Leu Phe Tyr Lys Leu Asp Val Ile Pro
    50                  55                  60

Ile Asp Ser Arg Asn Asn Ser Asn Asn Ser Thr Glu Phe Ser Ser Tyr
65                  70                  75                  80

Arg Leu Ile Ser Cys Asn Thr Ser Val Ile Thr Gln Ala
                85                  90

<210> SEQ ID NO 27
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Arg Leu Thr Pro Leu Cys Val Thr Leu Asn Cys Thr Ser Ala Asn
1               5                   10                  15

Leu Thr Asn Val Asn Asn Ile Thr Tyr Ala Pro Gly Ile Glu Lys Ile
            20                  25                  30

```
Thr Asp Glu Val Arg Asn Cys Ser Phe Asn Met Thr Thr Glu Ile Lys
        35                  40                  45

Asp Lys Lys Gln Lys Val Ser Ala Leu Phe Tyr Lys Leu Asp Ile Val
 50                  55                  60

Gln Ile Asn Ser Ser Lys Asn Ser Ser Glu Tyr Arg Leu Ile Asn Cys
 65                  70                  75                  80

Asn Thr Ser Val Ile Lys Gln Ala
                 85
```

<210> SEQ ID NO 28
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Ala Lys Leu Thr Pro Leu Cys Val Thr Leu Asn Cys Thr Asp Leu Lys
 1               5                  10                  15

Asn Asn Leu Leu Asn Thr Asn Ser Ser Ser Gly Glu Lys Met Glu Lys
                 20                  25                  30

Gly Glu Ile Lys Asn Cys Ser Phe Asn Ile Thr Thr Ser Ile Arg Asp
        35                  40                  45

Lys Val Gln Lys Glu Tyr Ala Leu Phe Tyr Lys Leu Asp Val Val Pro
 50                  55                  60

Ile Asp Asn Asn Asn Thr Ser Tyr Arg Leu Ile Ser Cys Asn Thr
 65                  70                  75                  80

Ser Val Ile Thr Gln Ala
                 85
```

<210> SEQ ID NO 29
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Val Lys Leu Thr Pro Leu Cys Val Thr Leu Asn Cys Thr Ala Ile Thr
 1               5                  10                  15

Asn Asp Thr Arg Gly Asn Glu Thr Gly Ile Asn Arg Thr Val Glu Thr
                 20                  25                  30

Thr Glu Met Thr Asn Cys Ser Phe Asn Met Thr Thr Glu Leu Arg Asp
        35                  40                  45

Arg Lys Lys Lys Val Asn Ala Leu Phe Tyr Lys Leu Asp Ile Val Gln
 50                  55                  60

Ile Gly Glu Asn Ser Ser Ser Gln Tyr Arg Leu Ile Asn Cys Asn Thr
 65                  70                  75                  80

Ser Val Ile Thr Gln Ala
                 85
```

<210> SEQ ID NO 30
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 30

Val Lys Leu Thr Pro Leu Cys Val Thr Leu Glu Cys Thr Gln Val Asn
1               5                   10                  15

Ala Thr Gln Gly Asn Thr Thr Gln Val Asn Val Thr Gln Val Asn Gly
                20                  25                  30

Asp Glu Met Lys Asn Cys Ser Phe Asn Thr Thr Thr Glu Ile Arg Asp
            35                  40                  45

Lys Lys Gln Lys Ala Tyr Ala Leu Phe Tyr Arg Leu Asp Leu Val Pro
        50                  55                  60

Leu Glu Arg Glu Asn Arg Gly Asp Ser Asn Ser Ala Ser Lys Tyr Ile
65                  70                  75                  80

Leu Ile Asn Cys Asn Thr Ser Ala Ile Thr Gln Ala
                85                  90

<210> SEQ ID NO 31
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Val Lys Leu Thr Pro Leu Cys Val Thr Leu His Cys Thr Asn Leu Glu
1               5                   10                  15

Asn Ala Thr Asn Thr Thr Ser Ser Asn Trp Lys Glu Met Asn Arg Gly
                20                  25                  30

Glu Ile Lys Asn Cys Ser Phe Asn Val Thr Thr Ser Ile Gly Asn Lys
            35                  40                  45

Met Gln Lys Glu Tyr Ala Leu Phe Tyr Lys Leu Asp Val Val Pro Ile
        50                  55                  60

Asp Asn Asp Asn Thr Ser Tyr Asn Leu Ile Asn Cys Asn Thr Ser Val
65                  70                  75                  80

Ile Thr Gln Ala

<210> SEQ ID NO 32
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Val Lys Leu Thr Pro Leu Cys Val Thr Leu Asn Cys Ser Asp Val Pro
1               5                   10                  15

Tyr Asn Gln Ser Thr Lys Tyr Asn Asp Asn Ser Thr Leu Tyr Asn Arg
                20                  25                  30

Glu Met Lys Asn Cys Ser Phe Asn Ala Thr Thr Glu Ile Lys Asp Lys
            35                  40                  45

Lys Lys Lys Glu Asn Ala Leu Phe Tyr Arg Leu Asp Val Val Pro Leu
        50                  55                  60

Gly Glu Ser Asn Ser Ser Thr Tyr Arg Leu Ile Asn Cys Asn Thr Ser
65                  70                  75                  80

Val Val Thr Gln Ala
                85
```

```
<210> SEQ ID NO 33
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Val Lys Leu Thr Pro Leu Cys Val Thr Leu His Cys Thr Asn Val Thr
1               5                   10                  15

Ile Ser Ser Thr Asn Gly Ser Thr Ala Asn Val Thr Met Arg Glu Glu
                20                  25                  30

Met Lys Asn Cys Ser Phe Asn Thr Thr Val Ile Arg Asp Lys Ile
            35                  40                  45

Gln Lys Glu Tyr Ala Leu Phe Tyr Lys Leu Asp Ile Val Pro Ile Glu
        50                  55                  60

Gly Lys Asn Thr Asn Thr Gly Tyr Arg Leu Ile Asn Cys Asn Thr Ser
65                  70                  75                  80

Val Ile Thr Gln Ala
                85

<210> SEQ ID NO 34
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Lys Leu Thr Pro Leu Cys Val Thr Leu Asn Cys Val Thr Tyr Asn
1               5                   10                  15

Asn Ser Met Asn Ser Ser Ala Thr Tyr Asn Asn Ser Met Asn Gly Glu
                20                  25                  30

Ile Lys Asn Cys Ser Phe Asn Thr Thr Thr Glu Leu Arg Asp Lys Lys
            35                  40                  45

Gln Lys Val Tyr Ala Leu Phe Tyr Arg Thr Asp Val Val Pro Leu Asn
        50                  55                  60

Asn Asn Asn Asn Asn Ser Glu Tyr Ile Leu Ile Asn Cys Asn Thr Ser
65                  70                  75                  80

Thr Ile Thr Gln Ala
                85

<210> SEQ ID NO 35
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Lys Leu Thr Pro Leu Cys Val Thr Leu Thr Cys Thr Asn Ala Lys
1               5                   10                  15

Asn Asp Asn Ala Thr Val Asp Gly Asn Ser Thr Thr Gly Gly Glu Ile
                20                  25                  30

Lys Asn Cys Ser Phe Asn Ile Thr Thr Glu Leu Arg Asp Lys Lys Gln
            35                  40                  45

Arg Val His Ala Leu Phe Tyr Arg Leu Asp Ile Val Pro Leu Asn Asn
        50                  55                  60
```

```
Ser Pro Arg Glu Lys Gly Gly Ser Ser Gln Tyr Arg Leu Ile Asn
65                  70                  75                  80

Cys Asn Thr Ser Ala Ile Thr Gln Thr
                85

<210> SEQ ID NO 36
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Val Lys Leu Thr Pro Leu Cys Val Thr Leu Asn Cys Thr Asp Glu Leu
1               5                   10                  15

Asn Asn Ser Asn Gly Thr Arg Val Asn Ile Thr Asp Lys Gly Glu Ile
                20                  25                  30

Lys Asn Cys Ser Phe Asn Val Thr Thr Ala Ile Arg Asp Lys Val Gln
            35                  40                  45

Lys Thr Tyr Ala Leu Phe Tyr Arg Leu Asp Val Val Pro Ile Asp Asp
        50                  55                  60

Lys His Asp Asn Ser Ser Asn Asn Ser Ser Arg Lys Tyr Arg Leu
65                  70                  75                  80

Ile Asn Cys Asn Thr Ser Val Ile Thr Gln Ala
                85                  90

<210> SEQ ID NO 37
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Val Gln Leu Thr Pro Leu Cys Val Thr Leu Asn Cys Thr Glu Leu Asn
1               5                   10                  15

Asn Asn Ser Thr Thr Thr Thr Asn Ser Ser Glu Gly Lys Glu Met Lys
                20                  25                  30

Asn Cys Ser Phe Asn Ile Pro Thr Ser Met Gln Asp Lys Thr Lys Lys
            35                  40                  45

Glu Tyr Ala Leu Phe Tyr Lys Leu Asp Ile Val Lys Ile Asp Asp Ser
        50                  55                  60

Asn Asn Ser Thr Asn Asn Ser Thr Tyr Arg Leu Ile Ser Cys Asn Thr
65                  70                  75                  80

Ser Val Val Thr Gln Ala
                85

<210> SEQ ID NO 38
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Val Lys Leu Thr Pro Leu Cys Val Thr Leu Thr Cys Thr Asn Thr Thr
1               5                   10                  15
```

```
Val Ser Asn Gly Ser Ser Asn Ser Asn Ala Asn Phe Glu Glu Met Lys
            20                  25                  30

Asn Cys Ser Phe Asn Ala Thr Thr Glu Ile Lys Asp Lys Lys Lys Asn
        35                  40                  45

Glu Tyr Ala Leu Phe Tyr Lys Leu Asp Ile Val Pro Leu Asn Asn Ser
    50                  55                  60

Ser Gly Lys Tyr Arg Leu Ile Asn Cys Asn Thr Ser Ala Ile Ala Gln
65                  70                  75                  80

Ala

<210> SEQ ID NO 39
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Val Lys Leu Thr Pro Leu Cys Val Thr Leu Glu Cys Lys Asn Val Asn
1               5                   10                  15

Ser Ser Ser Asp Thr Lys Asn Gly Thr Asp Pro Glu Met Lys Asn
            20                  25                  30

Cys Ser Phe Asn Ala Thr Thr Glu Leu Arg Asp Arg Lys Gln Lys Val
        35                  40                  45

Tyr Ala Leu Phe Tyr Lys Leu Asp Ile Val Pro Leu Asn Glu Lys Asn
    50                  55                  60

Ser Ser Glu Tyr Arg Leu Ile Asn Cys Asn Thr Ser Thr Ile Thr Gln
65                  70                  75                  80

Ala

<210> SEQ ID NO 40
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Val Lys Leu Thr Ser Leu Cys Val Thr Leu Lys Cys Ser Asn Phe Thr
1               5                   10                  15

Gly Lys Ser Asn Val Thr Tyr Lys Gly Asp Met Glu Val Lys Asn Cys
            20                  25                  30

Ser Phe Asn Val Thr Thr Glu Ile Arg Asp Lys Lys Gln Lys Val Tyr
        35                  40                  45

Ala Leu Phe Tyr Arg Leu Asp Ile Thr Pro Leu Asp Asp Asn Ser Ser
    50                  55                  60

Glu Tyr Ile Leu Ile Asn Cys Asn Ser Ser Thr Ile Thr Gln Ala
65                  70                  75

<210> SEQ ID NO 41
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41
```

```
Val Lys Leu Thr Pro Leu Cys Val Thr Leu Asn Cys Thr Thr Ala Ile
1               5                   10                  15

Ala His Asn Ala Ser Asn Gln Asn Ile Thr Asp Met Lys Ser Cys Ser
                20                  25                  30

Phe Asn Ala Thr Thr Glu Ile Arg Asp Lys His Lys Val Gln Ala
            35                  40                  45

Leu Phe Tyr Lys Leu Asp Ile Val Pro Leu Arg Glu Asn Glu Thr Asn
        50                  55                  60

Asn Ser Phe Thr Glu Tyr Arg Leu Ile Asn Cys Asn Thr Ser Ala Ile
65                  70                  75                  80

Thr Gln Ala

<210> SEQ ID NO 42
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Val Lys Leu Thr Pro Leu Cys Val Thr Leu Asn Cys Thr Asn Ala Thr
1               5                   10                  15

Ser Thr Asn Phe Thr Ala Lys Asn Glu Gly Gly Ile Lys Asn Cys Ser
                20                  25                  30

Phe Asn Ile Thr Thr Glu Arg Arg Gly Arg Lys Lys Thr Glu Tyr Ala
            35                  40                  45

Thr Phe Tyr Glu Thr Asp Leu Val Leu Ile Asn Asp Asp Asn Thr Thr
        50                  55                  60

Ser Tyr Arg Leu Ile Ser Cys Asn Thr Ser Val Ile Lys Gln Ala
65                  70                  75

<210> SEQ ID NO 43
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Val Lys Leu Thr Pro Leu Cys Val Thr Leu His Cys Thr Asn Val Thr
1               5                   10                  15

Ser Val Asn Thr Thr Gly Asp Arg Glu Gly Leu Lys Asn Cys Ser Phe
                20                  25                  30

Asn Met Thr Thr Glu Leu Arg Asp Lys Arg Gln Lys Val Tyr Ser Leu
            35                  40                  45

Phe Tyr Arg Leu Asp Ile Val Pro Ile Asn Glu Asn Gln Gly Ser Glu
        50                  55                  60

Tyr Arg Leu Ile Asn Cys Asn Thr Ser Ala Ile Thr Gln Ala
65                  70                  75

<210> SEQ ID NO 44
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

```
Val Lys Leu Thr Pro Leu Cys Val Thr Leu Asp Cys Asn Asn Val Thr
1               5                   10                  15

Asn Asn Gly Thr Ser Asp Met Arg Glu Ile Lys Asn Cys Ser Phe
            20                  25                  30

Asn Met Thr Thr Glu Leu Arg Asp Lys Arg Gln Lys Val Tyr Ser Leu
        35                  40                  45

Phe Tyr Lys Leu Asp Ile Val Gln Ile Asn Glu Asp Gln Gly Asn Ser
    50                  55                  60

Ser Asn Asn Lys Tyr Arg Leu Ile Thr Cys Asn Thr Ser Ala Ile Thr
65                  70                  75                  80

Gln Ala

<210> SEQ ID NO 45
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Val Lys Leu Thr Pro Leu Cys Val Thr Leu Asn Cys Ser Asp Ala Thr
1               5                   10                  15

Tyr Asn Asn Gly Thr Asn Ser Thr Asp Thr Met Lys Ile Cys Ser Phe
            20                  25                  30

Asn Ala Thr Thr Glu Leu Arg Asp Lys Lys Lys Lys Glu Tyr Ala Leu
        35                  40                  45

Phe Tyr Arg Leu Asp Ile Val Pro Leu Lys Asn Glu Ser Glu Ser Gln
    50                  55                  60

Asn Phe Ser Glu Tyr Ile Leu Ile Asn Cys Asn Thr Ser Thr Ile Ala
65                  70                  75                  80

Gln Ala

<210> SEQ ID NO 46
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Val Lys Leu Thr Pro Leu Cys Val Thr Leu Asn Cys Thr Asn Val Lys
1               5                   10                  15

Gly Asn Glu Ser Asp Thr Ser Glu Val Met Lys Asn Cys Ser Phe Lys
            20                  25                  30

Ala Thr Thr Glu Leu Lys Asp Lys Lys His Lys Val His Ala Leu Phe
        35                  40                  45

Tyr Lys Leu Asp Val Val Pro Leu Asn Gly Asn Ser Ser Ser Ser Gly
    50                  55                  60

Glu Tyr Arg Leu Ile Asn Cys Asn Thr Ser Ala Ile Thr Gln Ala
65                  70                  75

<210> SEQ ID NO 47
<211> LENGTH: 77
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 47

Val Lys Leu Thr Pro Leu Cys Val Thr Leu Glu Cys Gly Asn Ile Thr
1               5                   10                  15

Thr Arg Lys Glu Ser Met Thr Glu Met Lys Asn Cys Ser Phe Asn Ala
            20                  25                  30

Thr Thr Val Val Lys Asp Arg Lys Gln Thr Val Tyr Ala Leu Phe Tyr
        35                  40                  45

Lys Leu Asp Ile Val Pro Leu Ser Gly Lys Asn Ser Ser Gly Tyr Tyr
    50                  55                  60

Arg Leu Ile Asn Cys Asn Thr Ser Ala Ile Thr Gln Ala
65                  70                  75

<210> SEQ ID NO 48
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Val Lys Leu Thr Pro Leu Cys Val Thr Leu Arg Cys Thr Asn Ala Thr
1               5                   10                  15

Ile Asn Gly Ser Leu Thr Glu Glu Val Lys Asn Cys Ser Phe Asn Ile
            20                  25                  30

Thr Thr Glu Leu Arg Asp Lys Lys Gln Lys Ala Tyr Ala Leu Phe Tyr
        35                  40                  45

Arg Pro Asp Val Val Pro Leu Asn Lys Asn Ser Pro Ser Gly Asn Ser
    50                  55                  60

Ser Glu Tyr Ile Leu Ile Asn Cys Asn Thr Ser Thr Ile Thr Gln Ala
65                  70                  75                  80

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 49 cag aaa gaa tat gca ctt ttt tat aag ctt gat ata gta cca ata gat      48
Gln Lys Glu Tyr Ala Leu Phe Tyr Lys Leu Asp Ile Val Pro Ile Asp
1               5                   10                  15 aat                                                                  51
Asn

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Lys Glu Tyr Ala Leu Phe Tyr Lys Leu Asp Ile Val Pro Ile Asp
1               5                   10                  15

Asn

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)

<400> SEQUENCE: 51 ccc ccc gct agc gta aaa tta acc cca ctc                              30
Pro Pro Ala Ser Val Lys Leu Thr Pro Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Pro Ala Ser Val Lys Leu Thr Pro Leu
1               5                   10

<210> SEQ ID NO 53
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Ala Pro Gly Ser Ser Pro His His His His His Val Tyr Asn
1               5                   10                  15

Ile Thr Trp Glu Val Thr Asn Gly Asp Arg Glu Thr Val Trp Ala Ile
            20                  25                  30

Ser Gly Asn His Pro Leu Trp Thr Trp Trp Pro Val Leu Thr Pro Asp
        35                  40                  45

Leu Cys Met Leu Ala Leu Ser Gly Pro Pro His Trp Gly Leu Glu Tyr
    50                  55                  60

Gln Ala Pro Tyr Ser Ser Pro Pro Gly Pro Pro Cys Cys Ser Gly Ser
65                  70                  75                  80

Ser Gly Ser Ser Ala Gly Cys Ser Arg Asp Cys Asp Glu Pro Leu Thr
                85                  90                  95

Ser Leu Thr Pro Arg Cys Asn Thr Ala Trp Asn Arg Leu Lys Leu Asp
            100                 105                 110

Gln Val Thr His Lys Ser Ser Glu Gly Phe Tyr Val Cys Pro Gly Ser
        115                 120                 125

His Arg Pro Arg Glu Ala Lys Ser Cys Gly Gly Pro Asp Ser Phe Tyr
    130                 135                 140

Cys Ala Ser Trp Gly Cys Glu Thr Thr Gly Arg Val Tyr Trp Lys Pro
145                 150                 155                 160

Ser Ser Ser Trp Asp Tyr Ile Thr Val Asp Asn Asn Leu Thr Thr Ser
                165                 170                 175

-continued

```
Gln Ala Val Gln Val Cys Lys Asp Asn Lys Trp Cys Asn Pro Leu Ala
            180                 185                 190

Ile Gln Phe Thr Asn Ala Gly Lys Gln Val Thr Ser Trp Thr Thr Gly
        195                 200                 205

His Tyr Trp Gly Leu Arg Leu Tyr Val Ser Gly Arg Asp Pro Gly Leu
    210                 215                 220

Thr Phe Gly Ile Arg Leu Arg Tyr Gln Asn Leu Gly Pro Arg Val Pro
225                 230                 235                 240

Ile Gly Pro Asn Pro Val Leu Ala Asp Gln Leu Ser Leu Pro Arg Pro
                245                 250                 255

Asn Pro Leu Pro Lys Pro Ala Lys Ser Pro Pro Ala Ser Val Lys Leu
            260                 265                 270

Thr Pro Leu Cys Val Thr Leu Asn Cys Ile Asp Leu Arg Asn Ala Thr
        275                 280                 285

Asn Ala Thr Ser Asn Ser Asn Thr Thr Asn Thr Thr Ser Ser Ser Gly
    290                 295                 300

Gly Leu Met Met Glu Gln Gly Glu Ile Lys Asn Cys Ser Phe Asn Ile
305                 310                 315                 320

Thr Thr Ser Ile Arg Asp Lys Val Gln Lys Glu Tyr Ala Leu Phe Tyr
                325                 330                 335

Lys Leu Asp Ile Val Pro Ile Asp Asn Pro Lys Asn Ser Thr Asn Tyr
            340                 345                 350

Arg Leu Ile Ser Cys Asn Thr Ser Val Ile Thr Gln Ala
        355                 360                 365

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Lys Pro Ala Lys Ser Pro Pro Ala Ser Glu Asn Leu Tyr Phe Gln
1               5                   10                  15

Ser Ala Ser Val Lys Leu Thr Pro Leu Cys Val Thr
            20                  25

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Cys Asn Thr Ser Val Ile Thr Gln Ala
1               5                   10

<210> SEQ ID NO 56
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Ser Val Lys Leu Thr Pro Leu Cys Val Thr Leu Asn Cys Ile Asp
```

```
                1               5                   10                  15
Leu Arg Asn Ala Thr Asn Ala Thr Ser Asn Ser Asn Thr Thr Asn Thr
                20                  25                  30

Thr Ser Ser Ser Gly Gly Leu Met Met Glu Gln Gly Glu Ile Lys Asn
                35                  40                  45

Cys Ser Phe Asn Ile Thr Thr Ser Ile Arg Asp Lys Val Gln Lys Glu
            50                  55                  60

Tyr Ala Leu Phe Tyr Lys Leu Asp Val Val Pro Ile Asp Asn Pro Lys
65                      70                  75                  80

Asn Ser Thr Asn Tyr Arg Leu Ile Ser Cys Asn Thr Ser Val Ile Thr
                    85                  90                  95

Gln Ala

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Asn Leu Leu
1

<210> SEQ ID NO 58
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Thr Ser Arg Ile Asp Met Ala Cys Ser Thr Leu Pro Lys Ser Pro
1               5                   10                  15

Lys Asp Lys Ile Asp Pro Arg Asp Leu Leu Ile Pro Leu Ile Leu Phe
                20                  25                  30

Leu Ser Leu Lys Gly Ala Arg Ser Ala Ala Pro Gly Ser Ser Pro His
                35                  40                  45

His His His His Val Tyr Asn Ile Thr Trp Glu Val Thr Asn Gly
            50                  55                  60

Asp Arg Glu Thr Val Trp Ala Ile Ser Gly Asn His Pro Leu Trp Thr
65                      70                  75                  80

Trp Trp Pro Val Leu Thr Pro Asp Leu Cys Met Leu Ala Leu Ser Gly
                85                  90                  95

Pro Pro His Trp Gly Leu Glu Tyr Gln Ala Pro Tyr Ser Ser Pro Pro
                100                 105                 110

Gly Pro Pro Cys Cys Ser Gly Ser Ser Gly Ser Ala Gly Cys Ser
            115                 120                 125

Arg Asp Cys Asp Glu Pro Leu Thr Ser Leu Thr Pro Arg Cys Asn Thr
    130                 135                 140

Ala Trp Asn Arg Leu Lys Leu Asp Gln Val Thr His Lys Ser Ser Glu
145                 150                 155                 160

Gly Phe Tyr Val Cys Pro Gly Ser His Arg Pro Arg Glu Ala Lys Ser
                165                 170                 175

Cys Gly Gly Pro Asp Ser Phe Tyr Cys Ala Ser Trp Gly Cys Glu Thr
                180                 185                 190
```

```
Thr Gly Arg Val Tyr Trp Lys Pro Ser Ser Trp Asp Tyr Ile Thr
        195                 200                 205
Val Asp Asn Asn Leu Thr Thr Ser Gln Ala Val Gln Val Cys Lys Asp
    210                 215                 220
Asn Lys Trp Cys Asn Pro Leu Ala Ile Gln Phe Thr Asn Ala Gly Lys
225                 230                 235                 240
Gln Val Thr Ser Trp Thr Thr Gly His Tyr Trp Gly Leu Arg Leu Tyr
                245                 250                 255
Val Ser Gly Arg Asp Pro Gly Leu Thr Phe Gly Ile Arg Leu Arg Tyr
            260                 265                 270
Gln Asn Leu Gly Pro Arg Val Pro Ile Gly Pro Asn Pro Val Leu Ala
        275                 280                 285
Asp Gln Leu Ser Leu Pro Arg Pro Asn Pro Leu Pro Lys Pro Ala Lys
    290                 295                 300
Ser Pro Pro Ala Ser Val Lys Leu Thr Pro Leu Cys Val Thr Leu Asn
305                 310                 315                 320
Cys Ile Asp Leu Arg Asn Ala Thr Asn Ala Thr Ser Asn Ser Asn Thr
                325                 330                 335
Thr Asn Thr Thr Ser Ser Ser Gly Gly Leu Met Met Glu Gln Gly Glu
            340                 345                 350
Ile Lys Asn Cys Ser Phe Asn Ile Thr Thr Ser Ile Arg Asp Lys Val
        355                 360                 365
Gln Lys Glu Tyr Ala Leu Phe Tyr Lys Leu Asp Ile Val Pro Ile Asp
    370                 375                 380
Asn Pro Lys Asn Ser Thr Asn Tyr Arg Leu Ile Ser Cys Asn Thr Ser
385                 390                 395                 400
Val Ile Thr Gln Ala Gly Ala
                405

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Asn Leu Leu Lys Thr Gly Ser Gln
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Asn Asn Thr Thr Ser
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 61

Asn Thr Ser His Asp Lys
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Ile Leu Phe Ser Phe Gln Lys
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 63

His His His His His His
1               5
```